(12) United States Patent
Madhavan et al.

(10) Patent No.: US 10,294,505 B2
(45) Date of Patent: *May 21, 2019

(54) MICROORGANISM FOR PRODUCTION OF CHEMICALS DERIVED FROM ACETYL-COA

(71) Applicant: Mitsui Chemicals, Inc., Tokyo (JP)

(72) Inventors: Anjali Madhavan, Singapore (SG); Ryota Fujii, Chiba (JP); Tomonori Hidesaki, Singapore (SG); Su Sun Chong, Singapore (SG)

(73) Assignee: MITSUI CHEMCIALS, INC., Tokyo (JP)

( * ) Notice: Subject to any disclaimer, the term of this patent is extended or adjusted under 35 U.S.C. 154(b) by 519 days.

This patent is subject to a terminal disclaimer.

(21) Appl. No.: 14/428,611

(22) PCT Filed: Jan. 23, 2014

(86) PCT No.: PCT/JP2014/052013
§ 371 (c)(1),
(2) Date: Mar. 16, 2015

(87) PCT Pub. No.: WO2014/115896
PCT Pub. Date: Jul. 31, 2014

(65) Prior Publication Data
US 2015/0218607 A1 Aug. 6, 2015

(30) Foreign Application Priority Data
Jan. 24, 2013 (JP) ................................. 2013-011535

(51) Int. Cl.
| C12N 9/00 | (2006.01) |
| C12N 9/88 | (2006.01) |
| C12P 1/04 | (2006.01) |
| C12N 15/52 | (2006.01) |
| C12P 13/14 | (2006.01) |
| C12P 19/32 | (2006.01) |

(52) U.S. Cl.
CPC ............... *C12P 19/32* (2013.01); *C12N 9/88* (2013.01); *C12N 9/93* (2013.01); *C12N 15/52* (2013.01); *C12P 1/04* (2013.01); *C12P 13/14* (2013.01); *C12Y 401/03024* (2013.01); *C12Y 602/01009* (2013.01)

(58) Field of Classification Search
None
See application file for complete search history.

(56) References Cited

U.S. PATENT DOCUMENTS

| 6,331,419 B1 | 12/2001 | Moriya et al. |
| 7,015,010 B1 | 3/2006 | Izui et al. |
| 7,785,858 B2 | 8/2010 | Kozlov et al. |
| 2012/0149092 A1 | 6/2012 | Green et al. |
| 2014/0363847 A1 | 12/2014 | Fujii et al. |

FOREIGN PATENT DOCUMENTS

| DE | 1020070 59 248 A1 | 6/2009 | |
| EP | 0952221 A2 * | 10/1999 | ........... C12N 9/0016 |
| TW | 201311889 A1 | 3/2013 | |
| WO | WO-2008/020654 A1 | 2/2008 | |
| WO | WO-2009/046929 A2 | 4/2009 | |
| WO | WO-2009/094485 A1 | 7/2009 | |
| WO | WO-2010/071697 A1 | 6/2010 | |
| WO | WO-2011/099006 A2 | 8/2011 | |
| WO | WO-2013/018734 A1 | 2/2013 | |

OTHER PUBLICATIONS

Lawrence JG et al. Evolution of Coenzyme B12 Synthesis among Enteric Bacteria: Evidence for Loss and Reacquisition of a Multigene Complex. 1996. Genetics. 142:11-24 (Year: 1996).*
Office Action dated Mar. 21, 2017 in Taiwanese Patent Application No. 103102744.
Hara et al., "The complete genome sequence of *Pantoea ananatis* AJ13355, an organism with great biotechnological potential", Genomics, Transcriptomics, Proteomics, Appl Microbio Biotechnol (2012) 93, pp. 331-341.
Ivan A. Berg, "Ecological Aspects of the Distribution of Different Autotrophic $CO^2$ Fixation Pathways", Minireview, Applied and Environmental Microbiology, vol. 77, No. 6, Mar. 2011, pp. 1925-1936.
Intellectual Property Office of the Philippines Bureau of Patents, "Substantive Examination Report," issued in connection with Application No. Invention 1/2015/501540, dated Jun. 4, 2018.

* cited by examiner

*Primary Examiner* — Paul J Holland
(74) *Attorney, Agent, or Firm* — Foley & Lardner LLP

(57) ABSTRACT

Disclosed is an acetyl-CoA-producing microorganism, which is obtained by imparting malate thiokinase and malyl-CoA lyase enzymatic activities to a microorganism having none of the following (a), (b), (c) or (d), without imparting any of (a), (b), (c) or (d), or, even when one or more of (a), (b), (c) or (d) are imparted, not allowing the functions thereof to be exerted: (a) a carbon dioxide fixation cycle having an enzymatic reaction from malonyl-CoA to malonate semialdehyde or 3-hydroxypropionate, (b) a carbon dioxide fixation cycle having an enzymatic reaction from acetyl-CoA and $CO_2$ to pyruvate, (c) a carbon dioxide fixation cycle having an enzymatic reaction from crotonyl-CoA and $CO_2$ to ethylmalonyl-CoA or glutaconyl-CoA or (d) a carbon dioxide fixation cycle having an enzymatic reaction from $CO_2$ to formate.

6 Claims, No Drawings
Specification includes a Sequence Listing.

SEQUENCE LISTING

```
<160> NUMBER OF SEQ ID NOS: 20

<210> SEQ ID NO 1
<211> LENGTH: 33
<212> TYPE: DNA
<213> ORGANISM: Artificial Sequence
<220> FEATURE:
<223> OTHER INFORMATION: Primer for PCR

<400> SEQUENCE: 1
cgagctacat atgcaatgat tgacacgatt ccg                              33
```

<210> SEQ ID NO 2
<211> LENGTH: 32
<212> TYPE: DNA
<213> ORGANISM: Artificial Sequence
<220> FEATURE:
<223> OTHER INFORMATION: Primer for PCR

<400> SEQUENCE: 2
cgcgcgcatg ctatttgtta gtgaataaaa gg                                32

<210> SEQ ID NO 3
<211> LENGTH: 35
<212> TYPE: DNA
<213> ORGANISM: Artificial Sequence
<220> FEATURE:
<223> OTHER INFORMATION: Primer for PCR

<400> SEQUENCE: 3
ccgctcgagc atatgctgtc gcaatgattg acacg                             35

<210> SEQ ID NO 4
<211> LENGTH: 34
<212> TYPE: DNA
<213> ORGANISM: Artificial Sequence
<220> FEATURE:
<223> OTHER INFORMATION: Primer for PCR

<400> SEQUENCE: 4
gctattccat atgcagggtt attgtctcat gagc                              34

<210> SEQ ID NO 5
<211> LENGTH: 19
<212> TYPE: DNA
<213> ORGANISM: Artificial Sequence
<220> FEATURE:
<223> OTHER INFORMATION: Primer for PCR

<400> SEQUENCE: 5
tcggcacgta agaggttcc                                               19

<210> SEQ ID NO 6
<211> LENGTH: 19
<212> TYPE: DNA
<213> ORGANISM: Artificial Sequence
<220> FEATURE:
<223> OTHER INFORMATION: Primer for PCR

<400> SEQUENCE: 6
cgggtcgaat ttgctttcg                                               19

<210> SEQ ID NO 7
<211> LENGTH: 28
<212> TYPE: DNA
<213> ORGANISM: Artificial Sequence
<220> FEATURE:
<223> OTHER INFORMATION: Primer for PCR

<400> SEQUENCE: 7
ctagatctga cagtaagacg ggtaagcc                                     28

<210> SEQ ID NO 8
<211> LENGTH: 29
<212> TYPE: DNA
<213> ORGANISM: Artificial Sequence
<220> FEATURE:
<223> OTHER INFORMATION: Primer for PCR

```
<400> SEQUENCE: 8
ctagatctca gggttattgt ctcatgagc                                    29

<210> SEQ ID NO 9
<211> LENGTH: 45
<212> TYPE: DNA
<213> ORGANISM: Artificial Sequence
<220> FEATURE:
<223> OTHER INFORMATION: Primer for PCR

<400> SEQUENCE: 9
cctttggtta aaggctttaa gatcttccag tggacaaact atgcc                  45

<210> SEQ ID NO 10
<211> LENGTH: 45
<212> TYPE: DNA
<213> ORGANISM: Artificial Sequence
<220> FEATURE:
<223> OTHER INFORMATION: Primer for PCR

<400> SEQUENCE: 10
ggcatagttt gtccactgga agatcttaaa gcctttaacc aaagg                  45

<210> SEQ ID NO 11
<211> LENGTH: 32
<212> TYPE: DNA
<213> ORGANISM: Artificial Sequence
<220> FEATURE:
<223> OTHER INFORMATION: Primer for PCR

<400> SEQUENCE: 11
ggaattccat atggctgtta aaaatcgtct ac                                32

<210> SEQ ID NO 12
<211> LENGTH: 29
<212> TYPE: DNA
<213> ORGANISM: Artificial Sequence
<220> FEATURE:
<223> OTHER INFORMATION: Primer for PCR

<400> SEQUENCE: 12
gctctagatc agaatctgat tccgtgttc                                    29

<210> SEQ ID NO 13
<211> LENGTH: 963
<212> TYPE: DNA
<213> ORGANISM: Methylococcus capsulatus

<400> SEQUENCE: 13
atggctgtca agaaccgtct acaccgcagc gaactcgcgg tgccgggcag caatccacgc   60
atgctcgaga aagcgccgga agccggcgcc gacatcgtct ttctggacct ggaagatgcg  120
gttgcgccgg atgacaagga gcaagcgcgc cggaacatcg tcttcgcgct caacacctac  180
gactggtcca gatgcgcggt ctccgtccgc atcaacggcc tcgacaccca ttacgcctac  240
cgggacctcg ttgagatcgt cgagtcctgc ggcgacaagc tcgacaccat tctggtgccg  300
aaagtcggca gcgcctcgga cgttctgttc gtcgcgactt actttcccca gatcgaggcc  360
tacaaaggtt tcaaaccgat caatatccac gtgctgatcg aaacggccat gggcatggcc  420
aacgtggagg agatcgcccg cacctgtcct gaacgcatgg aggccatggt gttcggcgtg  480
gccgactacg ctgcgtcggt gcgcgccgcc acgaccaaca tcggcggcgc caacccggat  540
```

```
tacggcatgc tgaccgaccc tgacgaaagc ggtacccgcg cctatcactg ggccgaccag      600
tggcatttcg gcatttcccg catggtcgcg gcctgccgcg cctatgggct tcgccccatc      660
gacggcccct tcggcgattt cagcgatccg gaaggattcc gcgccgcagc ccgccgtgcc      720
gcggcactgg gctgcgaagg gaagtgggcg atccatccct cccagattcc actgtgcaac      780
gaaatcttca cacccacgga aaagaggtc acgcgggcct accgcatcct ggaagccatg       840
gagcaggcgg caaaggaggg caaaggcgcg gtgtctctgg atgggcggct gatcgatgcc      900
gcctcgatcc ggatggcgga aacgtggtc cgccagatga agcagatcga gtcgcgtcgg       960
tag                                                                   963

<210> SEQ ID NO 14
<211> LENGTH: 903
<212> TYPE: DNA
<213> ORGANISM: Methylococcus capsulatus

<400> SEQUENCE: 14
atgagcgtat tcgttaacaa gcactccaag gtcatcttcc agggcttcac cggcgagcac       60
gccaccttcc acgccaagga cgccatgcgg atgggcaccc gggtggtcgg cggtgtcacc      120
cctggcaaag gcggcacccg ccatcccgat cccgaactcg ctcatctgcc ggtgttcgac      180
accgtggctg aagccgtggc cgccaccggc gccgacgtct ccgccgtgtt cgtgccgccg      240
cccttcaatg cggacgcgtt gatggaagcc atagacgccg gcatccgggt cgccgtgacc      300
atcgccgacg gcatcccggt acacgacatg atccgactgc agcgctaccg ggtgggtaag      360
gattccatcg tgatcggacc gaacaccccc ggcatcatca cgccgggcga gtgcaaggtg      420
ggcatcatgc cttcgcacat ttacaagaag ggcaacgtcg gcatcgtgtc gcgctccggc      480
accctcaatt acgaggcgac ggaacagatg gccgcgcttg ggctgggcat caccacctcg      540
gtcggtatcg gcggtgaccc catcaacgga accgatttcg tcactgtcct gcgcgccttc      600
gaagccgacc cggaaaccga gatcgtggtg atgatcggcg aaatcggcgg ccccccaggaa    660 gtcgccgccg cccgctgggc caaggaaaac atgacaaagc cggtcatcgg cttcgtcgca      720
ggccttgccg caccgaccgg ccgacgcatg ggccatgccg cgccatcat ctccagcgag       780 gccgacaccg ccggagccaa gatggacgcc atggaagcct ggggctgta tgtcgcccgc       840 aacccggcac agatcggcca gaccgtgcta cgcgccgcgc aggaacacgg aatcagattc      900
tga                                                                   903

<210> SEQ ID NO 15
<211> LENGTH: 1170
<212> TYPE: DNA
<213> ORGANISM: Methylococcus capsulatus

<400> SEQUENCE: 15
gtgaatatcc atgagtacca ggccaaggag ctgctcaaga cctatggcgt gcccgtgccc       60
gacggcgccg ttgcctattc cgacgcgcag gccgccagcc tcgccgagga gatcggcggc      120
agccgctggg tggtcaaggc gcagatccat gccggcggtc gcgcaaggc cgggggcgta       180 aaggtcgccc actccatcga ggaagtccgc caatacgccg acgccatgct cggcagccac      240
ctcgtcaccc atcagaccgg cccgggaggc tcgctggttc agcgtctgtg ggtggaacag      300
gccagccata tcaaaaagga atactacctg ggcttcgtga tcgatcgcgg caatcaacgc      360
atcaccctga tcgcctccag cgagggcggc atggaaatcg aggaagtcgc aaaggaaacc      420
ccggagaaaa tcgtcaagga agtcgtcgat ccggccatag gcctgctgga cttccagtgc      480
```

```
cgcaaggtcg ccacggcgat cggcctgaaa ggcaaactga tgccccaggc cgtcaggctg    540
atgaaggcca tctaccgctg catgcgcgac aaagatgccc tgcaggccga aatcaatcct    600
ctggccatcg tgggcgaaag cgacgaatcg ctcatggtcc tggatgccaa gttcaacttc    660
gacgacaacg ccctgtaccg gcagcgcacc atcaccgaga tgcgcgacct ggccgaggaa    720
gacccgaaag aggtcgaagc ctccggccac ggtctcaatt acatcgccct cgacggcaac    780
atcggctgca tcgtcaatgg cgccggcctc gccatggctt cgctcgacgc catcaccctg    840
catggcggcc gtccggccaa cttcctcgac gtgggcggcg cgcctccccc cgagaaggtc    900
accaatgcct gccgcatcgt actggaagat cccaacgtcc gctgcatcct ggtcaacatc    960
tttgccggca tcaaccgctg tgactggatc gccaagggcc tgatccaggc ctgcgacagc   1020
ctgcagatca aggtgccgct gatcgtgcgc ctggccggga cgaacgtcga cgagggccgc   1080
aagatcctgg ccgaatccgg cctctccttc atcaccgcgg aaaatctgga cgacgcggcc   1140
gccaaggccg tcgccatcgt caagggataa                                     1170
```

<210> SEQ ID NO 16
<211> LENGTH: 320
<212> TYPE: PRT
<213> ORGANISM: Methylococcus capsulatus

<400> SEQUENCE: 16

```
Met Ala Val Lys Asn Arg Leu His Arg Ser Glu Leu Ala Val Pro Gly
1               5                   10                  15

Ser Asn Pro Arg Met Leu Glu Lys Ala Pro Glu Ala Gly Ala Asp Ile
            20                  25                  30

Val Phe Leu Asp Leu Glu Asp Ala Val Ala Pro Asp Asp Lys Glu Gln
        35                  40                  45

Ala Arg Arg Asn Ile Val Phe Ala Leu Asn Thr Tyr Asp Trp Ser Arg
    50                  55                  60

Cys Ala Val Ser Val Arg Ile Asn Gly Leu Asp Thr His Tyr Ala Tyr
65                  70                  75                  80

Arg Asp Leu Val Glu Ile Val Glu Ser Cys Gly Asp Lys Leu Asp Thr
                85                  90                  95

Ile Leu Val Pro Lys Val Gly Ser Ala Ser Asp Val Leu Phe Val Ala
            100                 105                 110

Thr Leu Leu Ser Gln Ile Glu Ala Tyr Lys Gly Phe Lys Pro Ile Asn
        115                 120                 125

Ile His Val Leu Ile Glu Thr Ala Met Gly Met Ala Asn Val Glu Glu
    130                 135                 140

Ile Ala Arg Thr Cys Pro Glu Arg Met Glu Ala Met Val Phe Gly Val
145                 150                 155                 160

Ala Asp Tyr Ala Ala Ser Val Arg Ala Arg Thr Thr Asn Ile Gly Gly
                165                 170                 175

Ala Asn Pro Asp Tyr Gly Met Leu Thr Asp Pro Asp Glu Ser Gly Thr
            180                 185                 190

Arg Ala Tyr His Trp Ala Asp Gln Trp His Phe Gly Ile Ser Arg Met
        195                 200                 205

Val Ala Ala Cys Arg Ala Tyr Gly Leu Arg Pro Ile Asp Gly Pro Phe
    210                 215                 220

Gly Asp Phe Ser Asp Pro Glu Gly Phe Arg Ala Ala Arg Arg Ala
225                 230                 235                 240

Ala Ala Leu Gly Cys Glu Gly Lys Trp Ala Ile His Pro Ser Gln Ile
```

```
                    245                 250                 255
Pro Leu Cys Asn Glu Ile Phe Thr Pro Thr Glu Lys Glu Val Thr Arg
            260                 265                 270

Ala Tyr Arg Ile Leu Glu Ala Met Glu Gln Ala Ala Lys Glu Gly Lys
        275                 280                 285

Gly Ala Val Ser Leu Asp Gly Arg Leu Ile Asp Ala Ala Ser Ile Arg
    290                 295                 300

Met Ala Glu Asn Val Val Arg Gln Met Lys Gln Ile Glu Ser Arg Arg
305                 310                 315                 320

<210> SEQ ID NO 17
<211> LENGTH: 300
<212> TYPE: PRT
<213> ORGANISM: Methylococcus capsulatus

<400> SEQUENCE: 17

Met Ser Val Phe Val Asn Lys His Ser Lys Val Ile Phe Gln Gly Phe
1               5                   10                  15

Thr Gly Glu His Ala Thr Phe His Ala Lys Asp Ala Met Arg Met Gly
            20                  25                  30

Thr Arg Val Val Gly Gly Val Thr Pro Gly Lys Gly Gly Thr Arg His
        35                  40                  45

Pro Asp Pro Glu Leu Ala His Leu Pro Val Phe Asp Thr Val Ala Glu
    50                  55                  60

Ala Val Ala Ala Thr Gly Ala Asp Val Ser Ala Val Phe Val Pro Pro
65                  70                  75                  80

Pro Phe Asn Ala Asp Ala Leu Met Glu Ala Ile Asp Ala Gly Ile Arg
                85                  90                  95

Val Ala Val Thr Ile Ala Asp Gly Ile Pro Val His Asp Met Ile Arg
            100                 105                 110

Leu Gln Arg Tyr Arg Val Gly Lys Asp Ser Ile Val Ile Gly Pro Asn
        115                 120                 125

Thr Pro Gly Ile Ile Thr Pro Gly Glu Cys Lys Val Gly Ile Met Pro
    130                 135                 140

Ser His Ile Tyr Lys Lys Gly Asn Val Gly Ile Val Ser Arg Ser Gly
145                 150                 155                 160

Thr Leu Asn Tyr Glu Ala Thr Glu Gln Met Ala Ala Leu Gly Leu Gly
                165                 170                 175

Ile Thr Thr Ser Val Gly Ile Gly Gly Asp Pro Ile Asn Gly Thr Asp
            180                 185                 190

Phe Val Thr Val Leu Arg Ala Phe Glu Ala Asp Pro Glu Thr Glu Ile
        195                 200                 205

Val Val Met Ile Gly Glu Ile Gly Gly Pro Gln Glu Val Ala Ala Ala
    210                 215                 220

Arg Trp Ala Lys Glu Asn Met Thr Lys Pro Val Ile Gly Phe Val Ala
225                 230                 235                 240

Gly Leu Ala Ala Pro Thr Gly Arg Arg Met Gly His Ala Gly Ala Ile
                245                 250                 255

Ile Ser Ser Glu Ala Asp Thr Ala Gly Ala Lys Met Asp Ala Met Glu
            260                 265                 270

Ala Leu Gly Leu Tyr Val Ala Arg Asn Pro Ala Gln Ile Gly Gln Thr
        275                 280                 285

Val Leu Arg Ala Ala Gln Glu His Gly Ile Arg Phe
    290                 295                 300
```

<210> SEQ ID NO 18
<211> LENGTH: 389
<212> TYPE: PRT
<213> ORGANISM: Methylococcus capsulatus

<400> SEQUENCE: 18

| Met | Asn | Ile | His | Glu | Tyr | Gln | Ala | Lys | Glu | Leu | Leu | Lys | Thr | Tyr | Gly |
|---|---|---|---|---|---|---|---|---|---|---|---|---|---|---|---|
| 1 | | | | 5 | | | | | 10 | | | | | 15 | |

Val Pro Val Pro Asp Gly Ala Val Ala Tyr Ser Asp Ala Gln Ala Ala
            20                  25                  30

Ser Val Ala Glu Glu Ile Gly Gly Ser Arg Trp Val Lys Ala Gln
        35                  40                  45

Ile His Ala Gly Gly Arg Gly Lys Ala Gly Gly Val Lys Val Ala His
    50                  55                  60

Ser Ile Glu Glu Val Arg Gln Tyr Ala Asp Ala Met Leu Gly Ser His
65                  70                  75                  80

Leu Val Thr His Gln Thr Gly Pro Gly Gly Ser Leu Val Gln Arg Leu
                85                  90                  95

Trp Val Glu Gln Ala Ser His Ile Lys Lys Glu Tyr Tyr Leu Gly Phe
            100                 105                 110

Val Ile Asp Arg Gly Asn Gln Arg Ile Thr Leu Ile Ala Ser Ser Glu
        115                 120                 125

Gly Gly Met Glu Ile Glu Glu Val Ala Lys Glu Thr Pro Glu Lys Ile
    130                 135                 140

Val Lys Glu Val Val Asp Pro Ala Ile Gly Leu Leu Asp Phe Gln Cys
145                 150                 155                 160

Arg Lys Val Ala Thr Ala Ile Gly Leu Lys Gly Lys Leu Met Pro Gln
                165                 170                 175

Ala Val Arg Leu Met Lys Ala Ile Tyr Arg Cys Met Arg Asp Lys Asp
            180                 185                 190

Ala Leu Gln Ala Glu Ile Asn Pro Leu Ala Ile Val Gly Glu Ser Asp
        195                 200                 205

Glu Ser Leu Met Val Leu Asp Ala Lys Phe Asn Phe Asp Asp Asn Ala
    210                 215                 220

Leu Tyr Arg Gln Arg Thr Ile Thr Glu Met Arg Asp Leu Ala Glu Glu
225                 230                 235                 240

Asp Pro Lys Glu Val Glu Ala Ser Gly His Gly Leu Asn Tyr Ile Ala
                245                 250                 255

Leu Asp Gly Asn Ile Gly Cys Ile Val Asn Gly Ala Gly Leu Ala Met
            260                 265                 270

Ala Ser Leu Asp Ala Ile Thr Leu His Gly Gly Arg Pro Ala Asn Phe
        275                 280                 285

Leu Asp Val Gly Gly Gly Ala Ser Pro Glu Lys Val Thr Asn Ala Cys
    290                 295                 300

Arg Ile Val Leu Glu Asp Pro Asn Val Arg Cys Ile Leu Val Asn Ile
305                 310                 315                 320

Phe Ala Gly Ile Asn Arg Cys Asp Trp Ile Ala Lys Gly Leu Ile Gln
                325                 330                 335

Ala Cys Asp Ser Leu Gln Ile Lys Val Pro Leu Ile Val Arg Leu Ala
            340                 345                 350

Gly Thr Asn Val Asp Glu Gly Arg Lys Ile Leu Ala Glu Ser Gly Leu
        355                 360                 365

Ser Phe Ile Thr Ala Glu Asn Leu Asp Asp Ala Ala Lys Ala Val
    370                 375                 380

```
Ala Ile Val Lys Gly
385

<210> SEQ ID NO 19
<211> LENGTH: 34
<212> TYPE: DNA
<213> ORGANISM: Artificial Sequence
<220> FEATURE:
<223> OTHER INFORMATION: Primer for PCR

<400> SEQUENCE: 19
ctactagtct gtcgcaatga ttgacacgat tccg                                    34

<210> SEQ ID NO 20
<211> LENGTH: 48
<212> TYPE: DNA
<213> ORGANISM: Artificial Sequence
<220> FEATURE:
<223> OTHER INFORMATION: Primer for PCR

<400> SEQUENCE: 20
gctcgaattc ccatatgttc caccagctat ttgttagtga ataaaagg                     48
```

MICROORGANISM FOR PRODUCTION OF CHEMICALS DERIVED FROM ACETYL-COA

CROSS REFERENCE TO RELATED APPLICATIONS

This application is the National Phase of PCT/JP2014/052013, filed Jan. 23, 2014, which claims priority to Japanese Application No. 2013-011535, filed Jan. 24, 2013.

TECHNICAL FIELD

The present invention relates to an acetyl-CoA-producing microorganism capable of producing chemicals derived from acetyl-CoA, for example L-glutamic acid, with high-yield and productivity by the introduction of a carbon dioxide fixation pathway.

BACKGROUND ART

Acetyl-CoA is an extremely important intermediate in metabolic pathways of microorganisms. Various metabolites are produced via acetyl-CoA. Known examples of such substances produced via acetyl-CoA include amino acids such as L-glutamic acid, L-glutamine, L-proline, L-arginine, L-leucine and L-isoleucine; organic acids such as acetic acid, propionic acid, butyric acid, caproic acid, citric acid, 3-hydroxybutyric acid, 3-hydroxyisobutyric acid, 3-aminoisobutyric acid, 2-hydroxyisobutyric acid, methacrylic acid and poly-3-hydroxybutyric acid; alcohols such as isopropyl alcohol, ethanol and butanol; acetone; and polyglutamic acid.

L-Glutamic acid, or 2-aminopentanedioic acid, is a naturally occurring amino acid and a constituent of fermented foods like soy sauce, fish sauce, fermented bean paste and cheese. The sodium salt of glutamic acid, known as monosodium glutamate or MSG, is widely used in the food industry as a seasoning agent.

A promising candidate for industrial glutamic acid production is the Gram negative bacterium belonging to the genus *Pantoea* from the Enterobacteriaceae family. In addition to producing high glutamic acid titers, the bacterium *Pantoea ananatis* is also resistant to high concentrations of glutamic acid and can grow at acidic pH (Appl. Microbiol. Biotechnol. 93:331-341 (2012)). With the establishment of genetic manipulation techniques for *P. ananatis*, superior recombinant strains have been successfully developed that demonstrate substantially higher glutamic acid production capacities (U.S. Pat. No. 6,331,419B1, U.S. Pat. No. 7,015,010B1).

In *P. ananatis*, a carbon source like glucose is metabolized via the Embden-Meyerhof-Parnas pathway to form pyruvate. Subsequently, acetyl-CoA is formed from pyruvate by the action of pyruvate dehydrogenase and/or pyruvate formate lyase with the concomitant loss of valuable carbon derived from the sugar in the form of by-products like carbon dioxide and/or formate. Thereafter, glutamic acid is produced from acetyl-CoA via the Krebs cycle intermediate 2-oxoglutarate. Naturally, in this pathway, the maximum yield of glutamic acid that can be achieved is limited by the inherent loss of carbon as carbon dioxide and thus, engineering an alternate pathway that can circumvent this loss and/or cause the fixation of carbon dioxide into the pathway can help to improve the overall yield, efficiency and economics of the fermentation process.

There are several known pathways in which carbon dioxide is fixed to provide a carbon source in microorganisms (Appl. Environ. Microbiol. 77(6), 1925-1936(2011)). Specific examples of the pathways include the Calvin-Benson cycle, reductive TCA cycle, Wood-Ljungdahl pathway, 3-hydroxypropionate cycle and 4-hydroxybutyrate cycle. The Calvin-Benson cycle is a $CO_2$ fixation pathway existing in plants and photosynthetic bacteria, and composed of about 12 kinds of enzymes, wherein $CO_2$ is fixed by ribulose-1,5-bisphosphate carboxylase (RubisCO) to produce glyceraldehyde 3-phosphate. The reductive TCA cycle is a cycle found in anaerobic bacteria and microaerophilic bacteria including green sulfur bacteria, and composed of 11 kinds of enzymes. The cycle is characterized by $CO_2$ fixation enzymes using ferredoxin as a coenzyme (acetyl-CoA carboxylase, 2-oxoglutarate synthase), and pyruvate is produced from $CO_2$ by a reaction in the reverse direction of the normal TCA cycle. The Wood-Ljungdahl pathway is a pathway found in anaerobic microorganisms such as acetic acid-producing bacteria, and composed of 9 kinds of enzymes, wherein $CO_2$ and formate on a coenzyme are reduced by formate dehydrogenase, CO dehydrogenase and the like to finally achieve conversion to acetyl-CoA. The 3-hydroxypropionate cycle is found in *Chloroflexus* bacteria and the like, and composed of 13 kinds of enzymes, wherein $CO_2$ is fixed by the action of acetyl-CoA (propionyl-CoA) carboxylase and acetyl-CoA is produced via malonyl-CoA and the like. The 4-hydroxybutyrate cycle is a pathway existing in archaebacteria and the like. In this cycle, $CO_2$ is fixed by the reactions of pyruvate synthase, acetyl-CoA (propionyl-CoA) carboxylase and phosphoenolpyruvate carboxylase, and acetyl-CoA is produced via 4-hydroxybutyryl-CoA and the like.

U.S. Pat. No. 7,785,858B2 patent document describes the engineering of an alternate pathway for acetyl-CoA formation with reduced production of carbon dioxide by enhancing the activity of the Bifidum pathway enzymes D-xylulose-5-phosphate phosphoketolase and/or fructose-6-phosphate phosphoketolase. As a result, theoretically, 1 mole of $CO_2$ can be saved per mole of glucose that is consumed via this alternative route. When this pathway was introduced to a glutamic acid-producing strain of *P. ananatis*, the glutamic acid titer increased by 2.6 g/L which corresponded to a 6% increase in overall glutamic acid yield.

On the other hand, several reports have been made as ideas attempting to introduce a pathway for fixation of carbon dioxide to a useful-compound-producing microorganism in order to produce a useful substance. For example, WO2009/094485 and WO2010/071697 disclose proposals to use a microorganism to which a pathway similar to the Wood-Ljungdahl pathway in acetic acid bacteria was introduced, in order to produce acetyl-CoA from carbon dioxide. Further, as an example of production of a useful compound by fixation of $CO_2$, WO2009/046929 discloses an attempt to use a microorganism to which hydrogenase and tetrahydrofolate lyase were introduced, in order to produce lactic acid from carbon dioxide. Further, WO2011/099006 proposes a cycle in which $CO_2$ is fixed via a reaction for fixation of carbon dioxide on acetyl-CoA and a reduction reaction of malonyl-CoA. DE 102007059248 A proposes production of acetyl-CoA by a pathway similar to the 4-hydroxybutyrate cycle.

SUMMARY OF THE INVENTION

Technical Problem

As described above, it can be said that ideally for fixing $CO_2$ and allowing conversion to acetyl-CoA, (a) the activity of each enzyme constituting the pathway should be sufficiently high; (b) no enzyme contained in the cycle should consume acetyl-CoA; and (c) the number of enzymes additionally imparted should be small and the cycle should be simple. However, none of the examples for production of acetyl-CoA or chemicals derived from acetyl-CoA via fixation of $CO_2$ reported so far have satisfied all of the conditions (a) to (c), and all such examples have been poorly realized.

In order to make the industrial production of chemicals derived from acetyl-CoA more cost competitive, higher product titers and yields are desirable. Hence, there is a need for engineering an efficient and highly active pathway for conversion of glucose to acetyl-CoA or chemicals derived from acetyl-CoA via fixation of $CO_2$. Any observed increase in the yield of chemicals derived from acetyl-CoA, such as glutamic acid, during fermentation would in effect be indicative of increase in yield of its precursor acetyl-CoA. Thus, one way to determine the effectiveness of an introduced $CO_2$ fixation pathway for increasing the yield of acetyl-CoA is to observe the effect on yield of acetyl-CoA-derived products like glutamic acid.

Another equally important aspect from an industrial point of view is to minimize the formation of waste products which would otherwise require additional costs for purification, recycling or disposal. Waste products could include byproduct chemicals, precipitated salts, cell mass and debris and the like contaminating the product stream. Any reduction in formation of such chemicals or biological waste products during fermentation is highly advantageous to reduce costs for downstream processing, recycling or disposal.

The present invention was made under the above-described circumstances and aims to provide a microorganism belonging to the genus *Pantoea* that is useful for high-yield production of acetyl-CoA and chemicals derived from acetyl-CoA, such as glutamic acid, by introduction of an efficient carbon dioxide fixation pathway. In other words, the present invention aims to provide a microorganism that is a bacterium of the genus *Pantoea* having a carbon dioxide fixation pathway capable of converting carbon dioxide to useful metabolites via acetyl-CoA with high-yield and efficiency and reduced byproducts. The invention also aims to provide a method for producing a useful metabolite, in which the microorganism is used.

Solution to Problem

More specifically, aspects of the present invention include the following.

<1> An acetyl-CoA-producing microorganism of the genus *Pantoea* which is obtained by imparting malate thiokinase and malyl-CoA lyase enzymatic activities to a microorganism having none of the following (a), (b), (c) or (d), without imparting any of (a), (b), (c) or (d), or, even when one or more of (a), (b), (c) or (d) are imparted, not allowing the functions thereof to be exerted:
  (a) a carbon dioxide fixation cycle having an enzymatic reaction from malonyl-CoA to malonate semialdehyde or 3-hydroxypropionate;
  (b) a carbon dioxide fixation cycle having an enzymatic reaction from acetyl-CoA and $CO_2$ to pyruvate;
  (c) a carbon dioxide fixation cycle having an enzymatic reaction from crotonyl-CoA and $CO_2$ to ethylmalonyl-CoA or glutaconyl-CoA; and
  (d) a carbon dioxide fixation cycle having an enzymatic reaction from $CO_2$ to formate.

<2> A method for producing acetyl-CoA, comprising the steps of: culturing the acetyl-CoA-producing microorganism described in <1> in contact with a carbon source material; and collecting a target product obtained by the contact.
<3> The method of producing acetyl-CoA described in <2>, further comprising the step of: supplying at least one selected from the group consisting of a carbonate ion, a hydrogen carbonate ion, a carbon dioxide gas and a reducing agent to a culture medium used for the culturing.
<4> The method of producing acetyl-CoA described in <2> or <3>, further comprising the step of: collecting a carbon dioxide-containing gas generated by the culturing, and supplying the gas to a culture medium used for the culturing.
<5> A method for producing glutamic acid, comprising the steps of: culturing the acetyl-CoA-producing microorganism described in <1> in contact with a carbon source material; and collecting glutamic acid obtained by the contact Advantageous Effects of Invention According to the present invention, a microorganism belonging to the genus *Pantoea* that is useful for high-yield production of chemicals derived from acetyl-CoA, such as glutamic acid, by introduction of an efficient carbon dioxide fixation pathway can be provided, and a method for producing acetyl-CoA or a useful metabolite like glutamic acid using the microorganism can also be provided. In other words, according to the present invention, a microorganism that is a bacterium of the genus *Pantoea* having a carbon dioxide fixation pathway capable of converting carbon dioxide to useful metabolites via acetyl-CoA with high efficiency can be provided. Further, according to the invention, a method for producing a useful metabolite, in which the microorganism is used, can be provided.

As an added advantage, the microorganism of the present invention generates less waste byproduct chemicals during fermentation, and therefore, the microorganism is highly advantageous to reduce costs for downstream processing, recycling or disposal. Further, the microorganism of the present invention generates less biomass in the waste stream which has significant implications in reducing waste recycling or disposal costs for an industrial process.

DESCRIPTION OF EMBODIMENTS

The acetyl-CoA-producing microorganism of the present invention is an acetyl-CoA-producing microorganism of the genus *Pantoea* which is obtained by imparting malate thiokinase and malyl-CoA lyase enzymatic activities to a microorganism having none of the following (a), (b), (c) or (d), without imparting any of (a), (b), (c) or (d), or, even when one or more of (a), (b), (c) or (d) are imparted, not allowing the functions thereof to be exerted:
  (a) a carbon dioxide fixation cycle having an enzymatic reaction from malonyl-CoA to malonate semialdehyde or 3-hydroxypropionate;
  (b) a carbon dioxide fixation cycle having an enzymatic reaction from acetyl-CoA and $CO_2$ to pyruvate;
  (c) a carbon dioxide fixation cycle having an enzymatic reaction from crotonyl-CoA and $CO_2$ to ethylmalonyl-CoA or glutaconyl-CoA; and
  (d) a carbon dioxide fixation cycle having an enzymatic reaction from $CO_2$ to formate.

According to the present invention, by imparting enzymatic activity/activities, a carbon dioxide fixation cycle that fixes $CO_2$ produced in sugar metabolism or $CO_2$ supplied from outside is constructed, and an acetyl-CoA-producing microorganism having an acetyl-CoA production pathway which allows efficient conversion of $CO_2$ to acetyl-CoA can be provided.

That is, the present invention was accomplished by intensively studying conversion of $CO_2$ to acetyl-CoA and, as a result, discovering, as described above, that $CO_2$ can be converted to acetyl-CoA by imparting malate thiokinase and malyl-CoA lyase enzymatic activities to a microorganism having none of the following (a), (b), (c) or (d), without imparting any of (a), (b), (c) or (d), or, even when one or more of (a), (b), (c) or (d) are imparted, not allowing the functions thereof to be exerted:

(a) a carbon dioxide fixation cycle having an enzymatic reaction from malonyl-CoA to malonate semialdehyde or 3-hydroxypropionate;
(b) a carbon dioxide fixation cycle having an enzymatic reaction from acetyl-CoA and $CO_2$ to pyruvate;
(c) a carbon dioxide fixation cycle having an enzymatic reaction from crotonyl-CoA and $CO_2$ to ethylmalonyl-CoA or glutaconyl-CoA; and
(d) a carbon dioxide fixation cycle having an enzymatic reaction from $CO_2$ to formate.

Further, by using the acetyl-CoA-producing microorganism that converts $CO_2$ to acetyl-CoA, or by further imparting enzymatic activity/activities to the microorganism, acetyl-CoA and useful metabolites derived from acetyl-CoA such as substances including isopropyl alcohol, ethanol, acetone, citric acid, itaconic acid, acetic acid, butyric acid, (poly-)3-hydroxybutyric acid, 3-hydroxyisobutyric acid, 3-aminoisobutyric acid, 2-hydroxyisobutyric acid, methacrylic acid, (poly)glutamic acid, glutamine, arginine, ornithine, citrulline, leucine, isoleucine and proline can be efficiently produced.

The present invention is described below.

The term "$CO_2$ fixation" in the present invention means conversion of $CO_2$ produced in sugar metabolism or conversion of $CO_2$ supplied from outside to an organic compound. The $CO_2$ may also be $HCO_3^-$. In the present specification, "$CO_2$ fixation" may also be referred to as "carbon dioxide fixation".

The term "step" in the present specification includes not only independent steps. Even when a step cannot be clearly distinguished from other steps, the step is included in this term as long as the expected purpose of the step can be achieved. Further, in the present specification, each numerical range represented using "to" means the range having the numerical values described before and after the "to" as the minimum value and the maximum value, respectively.

In the present invention, when the amount of each component in a composition is mentioned and the composition contains plural substances corresponding to the each component, the amount means the total amount of the plural substances contained in the composition unless otherwise specified.

The "reduction" of an enzymatic activity in the present invention means a state where the activity of an enzyme is significantly reduced by the gene recombination technology applied to the gene encoding the enzyme, compared to the state before carrying out the treatment.

The "enhancement" of an "activity" in the present invention broadly means enhancement of various enzymatic activities in microorganisms compared to the activities before the enhancement.

The method of enhancement is not restricted as long as the activities of enzymes of microorganisms can be increased, and examples of the method include enhancement by an enzyme gene introduced from outside the cell, enhancement by increasing expression of an enzyme gene in the cell, and the combination of these methods.

Specific examples of the enhancement by an enzyme gene introduced from outside the cell include: introducing a gene encoding an enzyme having higher activity than the host-derived enzyme from outside the cell of the host microorganism by the gene recombination technology in order to add the enzymatic activity by the introduced enzyme gene or to replace the inherent enzymatic activity of the host with this enzymatic activity; increasing the number of the enzyme gene derived from the host or the enzyme gene from outside the cell to not less than 2; and the combination of these methods.

Specific examples of the enhancement by increasing expression of an enzyme gene in the microorganism include: introduction of a base sequence that increases expression of the enzyme gene from outside the host microorganism into the microorganism; replacement of the promoter of the enzyme gene retained in the genome of the host microorganism with another promoter to increase expression of the enzyme gene; and the combination of these methods.

The "imparting" of an "activity" in the present invention broadly means introduction of an enzyme gene from the outside into an organism wherein the gene for the subject enzyme cannot be found, to impart the activity of the subject enzyme. The method of imparting is not restricted as long as the activity of the subject enzyme can be imparted to the microorganism, and examples of the method include transformation with a plasmid having an enzyme gene, introduction of an enzyme gene into the genome, and the combination of these methods.

The promoter to be used for "enhancement" or "imparting" of an "activity" is not restricted as long as the promoter allows expression of the gene, and examples of the promoter include constitutive promoters and inducible promoters.

When whether or not the microorganism has the subject enzyme gene is to be determined, one may refer to, for example, the gene information for each strain registered in KEGG (Kyoto Encyclopedia of Genes and Genomes; /www.genome.jp) or NCBI (National Center for Biotechnology Information; www.ncbi.nlm.nih.gov). In the present invention, only the gene information registered in KEGG or NCBI is used.

In the present invention, the enzymatic activity can be imparted by introducing a gene encoding the enzyme from outside the cell of the host microorganism into the cell by the gene recombination technology. In this case, the species from which the enzyme gene to be introduced was derived may be either the same with or different from the species of the host cell.

Preparation of the genomic DNA necessary for introduction of the gene from outside the cell into the cell, cleavage and ligation of the DNA, transformation, PCR (Polymerase Chain Reaction), and designing and synthesis of oligonucleotides to be used as primers may be carried out by conventional methods known to those skilled in the art. These methods are described in, for example, Sambrook, J., et al., "Molecular Cloning A Laboratory Manual, Second Edition", Cold Spring Harbor Laboratory Press, (1989).

The term "by the gene recombination technology" in the present invention includes any cases as long as a base sequence is modified by insertion of another DNA to the base sequence of an inherent gene, or by replacement or deletion, or the combination of these, of a certain part of a gene. The modification may also be due to, for example, occurrence of a mutation.

The "host" in the present invention means a microorganism, belonging to the genus *Pantoea*, in a state where the effect of the present invention can be exerted, which state was realized by introduction of one or more genes from outside the microorganism.

The "host" in the present invention further means a microorganism, belonging to the genus *Pantoea*, that can have a capacity to produce acetyl-CoA from a carbon source material by using a certain means, irrespective of whether or not the microorganism inherently has the capacity to produce acetyl-CoA from a carbon source material.

The "host" in the present invention may have a pathway for production of a useful metabolite. The "useful metabolite" in the present invention is a general term for major metabolites in the metabolic pathways of microorganisms, such as alcohols, amino acids, organic acids and terpenes. The microorganism may be one having a capacity to produce a useful metabolite by using a certain means, irrespective of whether or not the microorganism inherently has a capacity to produce the useful metabolite.

The "useful metabolite derived from acetyl-CoA" in the present invention is a general term for useful metabolites produced via acetyl-CoA in metabolic pathways. In terms of alcohols, examples of the useful metabolite include isopropyl alcohol, ethanol and butanol. In terms of amino acids, examples of the useful metabolite include L-glutamic acid, L-glutamine, L-arginine, L-ornithine, L-citrulline, L-leucine and L-proline. In terms of organic acids, examples of the useful metabolite include 3-hydroxybutyric acid, poly-3-hydroxybutyric acid, polyglutamic acid, 3-hydroxyisobutyric acid, 3-aminoisobutyric acid, 2-hydroxyisobutyric acid, methacrylic acid, citric acid, acetic acid, propionic acid, butyric acid, caproic acid and mevalonic acid. In terms of terpenes, examples of the useful metabolite include isoprene, squalene, steroid and carotenoid. Other examples of the useful metabolite include acetone. The microorganism may be one having a capacity to produce a useful metabolite derived from acetyl-CoA by using a certain means, irrespective of whether or not the microorganism inherently has a capacity to produce the useful metabolite derived from acetyl-CoA.

The "production of acetyl-CoA" in the present invention means conversion of a certain substance to acetyl-CoA in a metabolic pathway. Since acetyl-CoA is a metabolic intermediate and quickly converted to various substances in metabolic pathways, the amount of acetyl-CoA apparently observed does not necessarily increase. However, the effect can be known indirectly by detection of a label derived from $CO_2$ in a substance derived from acetyl-CoA, by observation of an increase in the yield of a substance derived from acetyl-CoA relative to sugar consumption, or the like. Since various factors (e.g., the amounts of coenzymes, amounts of substrates, and metabolic changes due to feedback inhibition) are involved in the conversion, the amount of production of acetyl-CoA is not necessarily proportional to the amount of all substances derived from acetyl-CoA. However, if a production pathway from acetyl-CoA to a specific substance is enhanced or such a production pathway is inherently strong (for example, in the case of glutamic acid-producing microorganism described below), the conversion efficiency after acetyl-CoA is hardly affected by external factors, so that the production efficiency of the substance can be regarded as an index of the production efficiency of acetyl-CoA.

The acetyl-CoA-producing microorganism of the present invention is an acetyl-CoA-producing microorganism which is obtained by imparting malate thiokinase and malyl-CoA lyase enzymatic activities to a microorganism having none of the following (a), (b), (c) or (d), without imparting any of (a), (b), (c) or (d), or, even when one or more of (a), (b), (c) or (d) are imparted, not allowing the functions thereof to be exerted:

(a) a carbon dioxide fixation cycle having an enzymatic reaction from malonyl-CoA to malonate semialdehyde or 3-hydroxypropionate;
(b) a carbon dioxide fixation cycle having an enzymatic reaction from acetyl-CoA and $CO_2$ to pyruvate;
(c) a carbon dioxide fixation cycle having an enzymatic reaction from crotonyl-CoA and $CO_2$ to ethylmalonyl-CoA or glutaconyl-CoA; and
(d) a carbon dioxide fixation cycle having an enzymatic reaction from $CO_2$ to formate.

In view of the production efficiency of acetyl-CoA, the acetyl-CoA-producing microorganism is preferably imparted with the enzymatic activities of malate thiokinase and malyl-CoA lyase.

The term "does not (inherently) have" herein means that the host microorganism does not inherently have the cycle in the natural environment.

The "carbon dioxide fixation cycle having an enzymatic reaction from malonyl-CoA to malonate semialdehyde or 3-hydroxypropionate" in the present specification means the cycles (1) to (7) below:

(1) the cycle shown in FIG. 1 of WO2011/099006, wherein acetyl-CoA is converted via malonyl-CoA, 3-hydroxypropionate, propionyl-CoA, malic acid and malyl-CoA, again to acetyl-CoA;
(2) the cycle shown in FIG. 4A of WO2011/099006, wherein acetyl-CoA is converted via malonyl-CoA, malonate semialdehyde, β-alanine, malic acid and malyl-CoA, again to acetyl-CoA;
(3) the cycle shown in FIG. 4B, 16 or 18 of WO2011/099006, wherein acetyl-CoA is converted via malonyl-CoA, hydroxypropionate, (R)-lactate or (S)-lactate, malate and malyl-CoA, again to acetyl-CoA.
(4) the cycle shown in FIG. 8 of WO2011/099006, wherein acetyl-CoA is converted via malonyl-CoA, malonate semialdehyde or hydroxypropionate, pyruvate, malate and malyl-CoA, again to acetyl-CoA;
(5) the cycle shown in FIG. 9A, 9B or 9C of WO2011/099006, wherein acetyl-CoA is converted via malonyl-CoA, hydroxypropionate, 2-ketoglutarate, malate and malyl-CoA, again to acetyl-CoA;
(6) the cycle shown in FIG. 9D or 9F of WO2011/099006, wherein acetyl-CoA is converted via malonyl-CoA, hydroxypropionate, methylmalonyl-CoA, malate and malyl-CoA, again to acetyl-CoA; and
(7) the cycle shown in FIG. 17 of WO2011/099006, wherein acetyl-CoA is converted via malonyl-CoA, malonate semialdehyde or hydroxypropionate, methylmalonyl-CoA, pyruvate, oxaloacetate, malate and malyl-CoA, again to acetyl-CoA.

All of carbon dioxide fixation cycles (1) to (7) described above have an enzymatic reaction from malonyl-CoA to malonate semialdehyde or 3-hydroxypropionate. Such reactions are catalyzed by malonate semialdehyde dehydrogenase or malonyl-CoA reductase (WO2011/099006). It is said that such reduction reactions of a carboxylic acid or a (thio)ester thereof such as reduction of succinyl-CoA or reduction of malonyl-CoA are difficult as enzymatic reactions in general and should be avoided as much as possible in fermentation pathways (Atsumi et al., Nature, 451, (3), 86-89, 2008; Yim et al., Nat. Chem. Biol., 7, 445-452, 2011).

The "carbon dioxide fixation cycle having an enzymatic reaction from acetyl-CoA and $CO_2$ to pyruvate" in the present specification means the cycles (8) to (10) below:

(8) the cycle shown in FIG. 1 of WO2011/099006, wherein acetyl-CoA is converted via pyruvate, phosphoenolpyruvate, oxaloacetate, malate and malyl-CoA, again to acetyl-CoA;

(9) the cycle shown in FIG. 7C, 7D or 7E of WO2011/099006, wherein acetyl-CoA is converted via pyruvate, malate and malyl-CoA, again to acetyl-CoA; and

(10) the cycle shown in FIG. 9M of WO2011/099006, wherein acetyl-CoA is converted via pyruvate, 2-ketoglutarate, malate and malyl-CoA, again to acetyl-CoA.

All of carbon dioxide fixation cycles (8) to (10) have an enzymatic reaction from acetyl-CoA and $CO_2$ to pyruvate. This reaction is catalyzed by pyruvate synthase (WO2011/099006). The synthetic reaction of pyruvate by pyruvate synthase requires strong reducing power through ferredoxin; the reaction proceeds only slowly; and the reaction proceeds only under extreme anaerobic conditions because the reaction is sensitive to oxygen.

The "carbon dioxide fixation cycle having an enzymatic reaction from crotonyl-CoA and $CO_2$ to ethylmalonyl-CoA or glutaconyl-CoA" in the present specification means the cycle shown in FIG. 9H or 9J of WO2011/099006, wherein acetyl-CoA is converted via crotonyl-CoA, ethylmalonyl-CoA or glutaconyl-CoA, oxaloacetate, malate and malyl-CoA, again to acetyl-CoA.

The above-described conversion from crotonyl-CoA and $CO_2$ to ethylmalonyl-CoA or glutaconyl-CoA is catalyzed by crotonyl-CoA carboxylase/reductase or methylcrotonyl-CoA carboxylase. Since crotonyl-CoA carboxylase/reductase has high Km for carbonates (14 mM; PNAS 104(25) 10631-10636, (2007)), the activity cannot be expected in the low concentration range. Further, crotonyl-CoA as a substrate is produced from 3-hydroxybutyryl-CoA by dehydration reaction, and, in such an enzyme, hydration reaction, which is the reverse reaction, is predominant in a normal aqueous environment. Therefore, a sufficiently high rate cannot be expected. Further, the reported specific activity of methylcrotonyl-CoA carboxylase is not so high (0.2-0.6 U/mg; Arch Biochem Biophys. 310(1) 64-75 (1994)), and, similarly to the above case, a sufficiently high rate of production of crotonyl-CoA as a substrate cannot be expected, which is problematic.

The "carbon dioxide fixation cycle having an enzymatic reaction from $CO_2$ to formate" in the present specification means the cycle shown in FIG. 5, 6, 13 or 14 of WO2009/046929, that is, a cycle having a pathway wherein the reaction proceeds from $CO_2$ via formate and serine, and oxaloacetate is converted via malate, malyl-CoA and glycerate, again to oxaloacetate.

The enzymatic reaction from $CO_2$ to formate requires strong reducing power; the reaction proceeds only slowly; and the reaction proceeds only under extreme anaerobic conditions because the reaction is sensitive to oxygen.

In the present specification, the term "not allowing the function of the carbon dioxide fixation cycle to be exerted even if the carbon dioxide fixation cycle is imparted" means that the gene of an enzyme having an activity is introduced to a microorganism in which the subject enzyme gene is not found, in order to impart the activity of the subject enzyme, but the carbon dioxide fixation cycle is not functioning. The fact that "the carbon dioxide fixation cycle is not functioning" can be indirectly known, for example, by the fact that, in a test using a labeled $CO_2$, the label derived from $CO_2$ is not detected in metabolites in the cycle or substances derived from the metabolites, or by the fact that the yield of substances derived from metabolites in the cycle relative to sugar consumption does not increase.

The acetyl-CoA production pathway constructed in the acetyl-CoA-producing microorganism described above is a pathway containing malate thiokinase and malyl-CoA lyase. The acetyl-CoA production pathway does not have an enzyme that consumes acetyl-CoA, such as acetyl-CoA carboxylase or pyruvate synthase.

The enzymatic activities to be imparted to the microorganism of the genus *Pantoea* are not particularly restricted as long as malate thiokinase and malyl-CoA lyase enzymatic activities are imparted, and enzymatic activities with which the carbon dioxide fixation pathway in the invention can functionally be constructed may be selected, as appropriate, in accordance with the type of host microorganism.

The enzyme that consumes acetyl-CoA means an enzyme that uses acetyl-CoA as a substrate and allows conversion to another substance. Examples of the enzyme include acetyl-CoA carboxylase, which is classified as enzyme code number 6.4.1.2 according to the report of the enzyme commission of International Union of Biochemistry (I.U.B.) and converts acetyl-CoA to malonyl-CoA, and pyruvate synthase, which is classified as enzyme code number 1.2.7.1 and converts acetyl-CoA to pyruvate.

The malate thiokinase is classified as enzyme code number 6.2.1.9 according to the report of the enzyme commission of International Union of Biochemistry (I.U.B.), and is a general term for enzymes that bind malate to CoA to attain conversion to malyl-CoA. In this reaction, one molecule of ATP is consumed to produce one molecule each of ADP and phosphate. The enzyme is constituted by a large subunit of about 400 amino acids and a small subunit of 300 amino acids. In the gene, the large subunit is usually followed by the small subunit. In the present patent, for convenience, the large subunit is referred to as mtkB, and the small subunit is referred to as mtkA. The specific activity of this enzyme is reported to be, for example, 2.5 U/mg in terms of purified enzyme (Anal Biochem. 227(2), 363-367 (1995)).

This enzyme is mainly found in assimilation pathways for C1 carbon sources such as methane (J. Bacteriol. 176(23), 7398-7404 (1994)) and 3-hydroxypropionate pathways (Arch. Microbiol., 151, 252-256(1989)), and is characterized in that malyl-CoA lyase is present in the vicinity on the genome. Such an enzyme may be suitably used.

Examples of malate thiokinase include those derived from *Methylobacterium* such as *Methylobacterium extorquens*, those derived from *Hyphomicrobium* such as *Hyphomicrobium methylovorum* and *Hyphomicrobium denitrificans*, those derived from *Rhizobium* such as *Rhizobium* sp. NGR234, those derived from *Granulibacter* such as *Granulibacter bethesdensis*, those derived from *Nitrosomonas* such as *Nitrosomonas europaea*, those derived from *Methylococcus* such as *Methylococcus capsulatus*, and those derived from Gammaproteobacteria.

In view of the production efficiency of useful substances through acetyl-CoA, especially preferred examples of the amino acid sequence include the amino acid sequences derived from *Hyphomicrobium*, amino acid sequences derived from *Rhizobium*, amino acid sequences derived from *Nitrosomonas*, amino acid sequences derived from *Methylococcus*, and amino acid sequences derived from Gammaproteobacteria.

The malate thiokinase derived from *Hyphomicrobium*, malate thiokinase derived from *Rhizobium* and malate thiokinase derived from *Nitrosomonas* have homologies of 65% to 80% to each other. The malate thiokinase derived from

*Methylococcus* has homologies of 70% to 80% with the malate thiokinase derived from Gammaproteobacteria.

Malate thiokinase having a homology of not less than 70% with each of the amino acid sequences of malate thiokinase derived from *Hyphomicrobium*, malate thiokinase derived from *Rhizobium*, malate thiokinase derived from *Nitrosomonas*, malate thiokinase derived from *Methylococcus* and malate thiokinase derived from Gammaproteobacteria disclosed in the present invention, and having the malate thiokinase activity may be suitably used for the production of acetyl-CoA or a useful product derived from acetyl-CoA of the present invention.

As the gene for the malate thiokinase (mtk), DNA having a base sequence of the gene encoding malate thiokinase obtained from each of the above-mentioned source organisms or a synthetic DNA sequence synthesized based on a known base sequence thereof may be used.

Preferred examples of the DNA include DNAs having base sequences of the gene derived from *Methylobacterium* such as *Methylobacterium extorquens*, the gene derived from *Hyphomicrobium* such as *Hyphomicrobium methylovorum* and *Hyphomicrobium denitrificans*, the gene derived from *Rhizobium* such as *Rhizobium* sp. NGR234, the gene derived from *Granulibacter* such as *Granulibacter bethesdensis*, the gene derived from *Nitrosomonas* such as *Nitrosomonas europaea*, the gene derived from *Methylococcus* such as *Methylococcus capsulatus*, and the gene derived from Gammaproteobacteria.

In view of the production efficiency of acetyl-CoA, preferred examples of the DNA include DNAs having base sequences derived from *Hyphomicrobium*, base sequences derived from *Rhizobium*, base sequences derived from *Granulibacter*, base sequences derived from *Nitrosomonas*, base sequences derived from *Methylococcus*, and base sequences derived from Gammaproteobacteria.

Especially preferred examples of the base sequences include base sequences derived from *Hyphomicrobium*, base sequences derived from *Rhizobium* after codon optimization, base sequences derived from *Nitrosomonas*, base sequences derived from *Methylococcus*, and base sequences derived from Gammaproteobacteria.

The malyl-CoA lyase is an enzyme which is classified as enzyme code number 4.1.3.24 according to the report of the enzyme commission of International Union of Biochemistry (I.U.B.) and produces glyoxylate and acetyl-CoA from malyl-CoA. Examples of the enzyme include those derived from *Methylobacterium* such as *Methylobacterium extorquens*, *Hyphomicrobium* such as *Hyphomicrobium methylovorum* and *Hyphomicrobium denitrificans*, *Chloroflexus* such as *Chloroflexus aurantiacus*, *Nitrosomonas* such as *Nitrosomonas europaea*, and *Methylococcus* such as *Methylococcus capsulatus*.

In view of the production efficiency of acetyl-CoA, especially preferred examples of the amino acid sequence include an amino acid sequence derived from *Methylobacterium*, amino acid sequences derived from *Hyphomicrobium*, amino acid sequence derived from *Nitrosomonas*, and amino acid sequence derived from *Methylococcus*.

For example, the specific activity of malyl-CoA lyase in *Methylobacterium extorquens* is reported to be 28.1 U/mg in terms of purified enzyme (Biochem. J. 139, 399-405, (1974)).

As the gene for the malyl-CoA lyase (mcl), DNA having a base sequence of the gene encoding malyl-CoA lyase obtained from each of the above-mentioned source organisms or a synthetic DNA sequence synthesized based on a known base sequence thereof may be used. Preferred examples of the DNA include DNAs having base sequences of the gene derived from *Methylobacterium* such as *Methylobacterium extorquens*, the gene derived from *Hyphomicrobium* such as *Hyphomicrobium methylovorum* and *Hyphomicrobium denitrificans*, and the gene derived from *Chloroflexus* such as *Chloroflexus aurantiacus*. In view of the production efficiency of acetyl-CoA, especially preferred examples of the DNA include DNAs having base sequences of the gene derived from *Methylobacterium* and the gene derived from *Hyphomicrobium*.

Especially preferred examples of the base sequences of the gene derived from *Methylobacterium* include a base sequence of the gene derived from *Methylobacterium extorquens*; especially preferred examples of the base sequences of the gene derived from *Hyphomicrobium* include a base sequence of the gene derived from *Hyphomicrobium* methylovorum and a base sequence of the gene derived from *Hyphomicrobium denitrificans*; especially preferred examples of the base sequences of the gene derived from *Nitrosomonas* include a base sequence of the gene derived from *Nitrosomonas europaea*; and especially preferred examples of the base sequences of the gene derived from *Methylococcus* include a base sequence of the gene derived from *Methylococcus capsulatus*.

The acetyl-CoA carboxylase is classified as enzyme code number 6.4.1.2 according to the report of the enzyme commission of International Union of Biochemistry (I.U.B.), and is a general term for enzymes that convert acetyl-CoA and $CO_2$ to malonyl-CoA.

The malonate semialdehyde dehydrogenase is classified as enzyme code number 1.2.1.18 according to the report of the enzyme commission of International Union of Biochemistry (I.U.B.), and is a general term for enzymes that convert malonyl-CoA to malonate semialdehyde.

The malonyl-CoA reductase is a general term for enzymes that convert malonyl-CoA to malonate semialdehyde or 3-hydroxypropionate.

The crotonyl-CoA carboxylase/reductase is classified as enzyme code number 1.3.1.85 according to the report of the enzyme commission of International Union of Biochemistry (I.U.B.), and is a general term for enzymes that convert crotonyl-CoA to ethylmalonyl-CoA.

The methylcrotonyl-CoA carboxylase is classified as enzyme code number 6.4.1.4 according to the report of the enzyme commission of International Union of Biochemistry (I.U.B.), and is a general term for enzymes that convert crotonyl-CoA to glutaconyl-CoA.

The pyruvate synthase is classified as enzyme code number 1.2.7.1 according to the report of the enzyme commission of International Union of Biochemistry (I.U.B.), and is a general term for enzymes that convert acetyl-CoA to pyruvate.

The phosphoenolpyruvate carboxylase is classified as enzyme code number 4.1.1.31 according to the report of the enzyme commission of International Union of Biochemistry (I.U.B.), and is a general term for enzymes that convert phosphoenolpyruvate and carbon dioxide to oxaloacetate and phosphate. Examples of this enzyme include those derived from *Escherichia* bacteria such as *Escherichia coli*; *Pantoea* bacteria such as *Pantoea ananatis*; *Corynebacterium* bacteria such as *Corynebacterium glutamicum*; *Hyphomicrobium* bacteria such as *Hyphomicrobium methylovorum*; *Starkeya* bacteria such as *Starkeya novella*; *Rhodopseudomonas* bacteria such as *Rhodopseudomonas* sp.; and *Streptomyces* bacteria such as *Streptomyces coelicolor*.

As the gene for the phosphoenolpyruvate carboxylase (ppc), DNA having a base sequence of the gene encoding phosphoenolpyruvate carboxylase obtained from each of the above-mentioned source organisms or a synthetic DNA sequence synthesized based on a known base sequence thereof may be used. Preferred examples of the DNA include DNAs having base sequences of the gene derived from *Escherichia* bacteria such as *Escherichia coli*; *Pantoea* bacteria such as *Pantoea ananatis*; *Corynebacterium* bacteria such as *Corynebacterium glutamicum*; *Hyphomicrobium* bacteria such as *Hyphomicrobium methylovorum*; *Starkeya* bacteria such as *Starkeya novella*; *Rhodopseudomonas* bacteria such as *Rhodopseudomonas* sp.; and *Streptomyces* bacteria such as *Streptomyces coelicolor*.

The acetyl-CoA-producing microorganism may have, in addition to the pathway that converts acetyl-CoA to a useful metabolite, a pathway that produces another metabolite using acetyl-CoA as a raw material, or an enzymatic activity related to the pathway that produces another metabolite may be enhanced. By this, the useful metabolite derived from acetyl-CoA can be produced from a carbon source material and carbon dioxide, while the productivity of the useful metabolite derived from acetyl-CoA can be increased.

The microorganism used in the present invention is not restricted as long as the microorganism belongs to the genus *Pantoea*, and does not have any of (a), (b), (c), or (d) below:
(a) a carbon dioxide fixation cycle having an enzymatic reaction from malonyl-CoA to malonate semialdehyde or 3-hydroxypropionate;
(b) a carbon dioxide fixation cycle having an enzymatic reaction from acetyl-CoA and $CO_2$ to pyruvate;
(c) a carbon dioxide fixation cycle having an enzymatic reaction from crotonyl-CoA and $CO_2$ to ethylmalonyl-CoA or glutaconyl-CoA; and
(d) a carbon dioxide fixation cycle having an enzymatic reaction from $CO_2$ to formate.

Examples of representative strains of the *Pantoea* bacteria include *Pantoea ananatis*, *Pantoea stewartii*, *Pantoea agglomerans* and *Pantoea citrea*. Specific examples of the strains include the following.

*Pantoea ananatis* AJ13355 strain (FERM BP-6614)(EP 0952221 A)

*Pantoea ananatis* AJ13356 strain (FERM BP-6615)(EP 0952221 A)

Although these strains are described as *Enterobacter agglomerans* in EP 0952221 A, the strains were reclassified into *Pantoea ananatis* as described above based on base sequence analysis of 16S rRNA and the like.

Examples of the pathway for production of other metabolites using acetyl-CoA as a raw material include a pathway that produces glutamic acid from acetyl-CoA. A microorganism produced by using a microorganism having a pathway that efficiently produces glutamic acid (which may be hereinafter referred to as "glutamic acid-producing microorganism") as a host and imparting or enhancing, or inactivating or reducing, the above-described respective enzymatic activities may be one preferred example of the microorganism having a pathway that produces other metabolites or the microorganism whose enzyme activity involved in the pathway that produces the metabolites is enhanced.

The glutamic acid-producing microorganism may be any microorganism as long as introduction and modification of genes for imparting the glutamic acid-producing capacity are possible. The glutamic acid-producing microorganism may be more preferably a *Pantoea* bacterium to which the glutamic acid-producing capacity was preliminarily imparted, and, by this, glutamic acid can be more efficiently produced.

Examples of the method for imparting the glutamic acid-producing capacity to a microorganism include modifying the microorganism such that expression of the gene encoding an enzyme involved in biosynthesis of L-glutamic acid is increased and/or the gene is overexpressed. Examples of the L-glutamic acid biosynthetic enzyme include glutamate dehydrogenase, glutamine synthetase, glutamate synthase, isocitrate dehydrogenase, aconitate hydratase, citrate synthase, phosphoenolpyruvate carboxylase, pyruvate carboxylase, pyruvate dehydrogenase, pyruvate kinase, phosphoenolpyruvate synthase, enolase, phosphoglyceromutase, phosphoglycerate kinase, glyceraldehyde 3-phosphate dehydrogenase, triose phosphate isomerase, fructose bisphosphate aldolase, phosphofructokinase and glucose phosphate isomerase. Preferably, among these enzymes, one or more of citrate synthase, phosphoenolpyruvate carboxylase and glutamate dehydrogenase has an increased activity, and, more preferably, all of the three enzymes have enhanced activities.

Examples of such a glutamic acid-producing microorganism include a glutamic acid-producing microorganism described in Japanese Patent Application Laid-Open (JP-A) No. 2005-278643.

As the L-glutamic acid-producing microorganism, a microorganism having an ability to accumulate L-glutamic acid in an amount exceeding the saturation concentration of L-glutamic acid in a liquid medium when the microorganism was cultured under acidic conditions (this may be hereinafter referred to as the L-glutamic acid-accumulating capacity under acidic conditions) may be used. For example, a strain having increased resistance to L-glutamic acid in a low-pH environment may be obtained by the method described in EP 1078989 A, to impart the ability to accumulate L-glutamic acid in an amount exceeding the saturation concentration.

Specific examples of the microorganism inherently having the L-glutamic acid-accumulating capacity under acidic conditions include the *Pantoea ananatis* AJ13356 strain (FERM BP-6615) and AJ13601 strain (FERM BP-7207) (see EP 0952221 A for these strains). *Pantoea ananatis* AJ13356 was deposited with National Institute of Bioscience and Human-Technology, Agency of Industrial Science and Technology, Ministry of International Trade and Industry (present name: International Patent Organism Depositary, National Institute of Technology and Evaluation (IPOD, NITE); address: Tsukuba Central 6, 1-1-1 Higashi, Tsukuba, Ibaraki 305-8566, Japan) under accession No. FERM P-16645 on Feb. 19, 1998, and the deposition was converted to international deposition under the Budapest Treaty under accession No. FERM BP-6615 on Jan. 11, 1999. It should be noted that this strain was identified as *Enterobacter agglomerans* and deposited as *Enterobacter agglomerans* AJ13355 when the strain was first isolated, but, according to recent base sequence analysis of 16S rRNA and the like, the strain was reclassified as *Pantoea ananatis* (see Examples below). Further, although the later-mentioned strains AJ13356 and AJ13601 induced derived from AJ13355 were similarly deposited to the above depositary as *Enterobacter agglomerans*, these strains are described as *Pantoea ananatis* in the present specification. AJ13601 was deposited with National Institute of Bioscience and Human-Technology, Agency of Industrial Science and Technology, Ministry of International Trade and Industry (present name: International Patent Organism Depositary, National Institute of Technology and Evaluation (IPOD, NITE)) under accession No. FERM P-17156 on Aug. 18, 1999, and the deposition was converted to international deposition under the Budapest Treaty under accession No. FERM BP-7207 on Jul. 6, 2000.

Other examples of the method for imparting or enhancing the L-glutamic acid-producing capacity include a method wherein resistance to an organic acid analogue or respiratory inhibitor is imparted, and a method wherein sensitivity to an inhibitor of cell wall synthesis is imparted. Specific examples of the method include a method wherein resistance to monofluoroacetic acid is imparted (JP 50-113209 A), method wherein resistance to adenine or resistance to thymine is imparted (JP 57-065198 A), method wherein urease is weakened (JP 52-038088 A), method wherein resistance to malonic acid is imparted (JP 52-038088 A), method wherein resistance to benzopyrone or naphthoquinones is imparted (JP 56-1889 A), method wherein resistance to HOQNO is imparted (JP 56-140895 A), method wherein resistance to α-ketomalonic acid is imparted (JP 57-2689 A), method wherein resistance to guanidine is imparted (JP 56-35981 A), and method wherein resistance to penicillin is imparted (JP 4-88994 A).

Specific examples of such resistant microorganisms include the following strains.

*Brevibacterium flavum* AJ3949 (FERM BP-2632; see JP 50-113209A)
*Corynebacterium glutamicum* AJ11628 (FERM P-5736; see JP 57-065198 A)
*Brevibacterium flavum* AJ11355 (FERM P-5007; see JP 56-1889 A)
*Corynebacterium glutamicum* AJ11368 (FERM P-5020; see JP 56-1889 A)
*Brevibacterium flavum* AJ11217 (FERM P-4318; see JP 57-2689 A)
*Corynebacterium glutamicum* AJ11218 (FERM P-4319; see JP 57-2689 A)
*Brevibacterium flavum* AJ11564 (FERM P-5472; see JP 56-140895 A)
*Brevibacterium flavum* AJ11439 (FERM P-5136; see JP 56-35981 A)
*Corynebacterium glutamicum* H7684 (FERM BP-3004; see JP 04-88994 A)
*Brevibacterium lactofermentum* AJ11426 (FERM P-5123; see JP 56-048890 A)
*Corynebacterium glutamicum* AJ11440 (FERM P-5137; see JP 56-048890 A)
*Brevibacterium lactofermentum* AJ11796 (FERM P-6402; see JP 58-158192 A)

Examples of the microorganisms inherently having mtk and mcl include methanotrophic microorganisms such as *Methylobacterium extorquens*. Since vector systems suitable for methanotrophic microorganisms or techniques for modification of genomic genes of methanotrophic microorganisms have not been developed, genetic manipulation of these microorganisms is more difficult than microorganisms such as *Pantoea*. Further, these microorganisms often grow slowly and therefore are not suitable for production of useful metabolites.

The method for production of acetyl-CoA or glutamic acid of the present invention includes use of the acetyl-CoA-producing microorganism to produce acetyl-CoA or glutamic acid as the product of interest from a carbon source material. That is, the method for producing acetyl-CoA includes: bringing the acetyl-CoA-producing microorganism into contact with a carbon source material and performing culture (hereinafter referred to as the culturing step); and recovering the product of interest (acetyl-CoA or glutamic acid) obtained by the contact (hereinafter referred to as the recovering step).

According to the method for producing acetyl-CoA, since the acetyl-CoA-producing microorganism is brought into contact with a carbon source material when the microorganism is cultured, the carbon source material is assimilated by the acetyl-CoA-producing microorganism, and the product of interest can be efficiently produced while carbon dioxide is fixed.

The carbon source material is not restricted as long as the material contains a carbon source that can be assimilated by the microorganism, and the material is preferably a plant-derived material.

Examples of the plant-derived material include parts such as a root, stem, trunk, branch, leaf, flower and seed; plant bodies containing the parts; and decomposed products of the plant parts. Further, among carbon sources obtained from plant bodies, plant parts and decomposed products thereof, those which can be utilized as carbon sources in culture of microorganisms are also included in the plant-derived material.

Examples of carbon sources included in the plant-derived material generally include sugars such as starch, sucrose, glucose, fructose, galactose, mannose, xylose and arabinose; decomposition products of herbaceous and woody materials containing large amounts of these components; cellulose hydrolysates; and combinations thereof. Further, glycerin and fatty acids derived from vegetable oils may also be included in the carbon source in the present invention.

Preferred examples of the plant-derived material include crops such as cereals; maize; rice; wheat; soybean; sugar cane; beet; cotton; and combinations thereof. Examples of the mode of use of the raw materials include, but are not limited to, raw products, juices and ground products. The carbon source may also be used as it is.

In the culturing step, the acetyl-CoA-producing microorganism is generally brought into contact with a plant-derived material by culturing the acetyl-CoA-producing microorganism in a medium containing the plant-derived material.

The contact density at which the plant-derived material is brought into contact with the acetyl-CoA-producing microorganism varies depending on the activity of the acetyl-CoA-producing microorganism, and the concentration of the plant-derived material in the medium may be generally not more than 20% by mass in terms of the initial sugar concentration calculated by conversion into glucose, with respect to the total mass of the mixture. In view of glucose tolerance of the acetyl-CoA-producing microorganism, the initial sugar concentration may be preferably not more than 15% by mass. Other components are not restricted as long as the components are added in the amounts usually employed for culture media for microorganisms.

The method of producing acetyl-CoA or glutamic acid may further include supplying a carbonate ion, a hydrogen carbonate ion, a carbon dioxide gas ($CO_2$ gas) and/or a reducing agent to a culture medium used for the culturing (hereinafter referred to as "supply process"). Regarding the conditions in the supply process such as temperature or pH, the same conditions as those in the culture process may be applied.

Supply of a carbonate ion, a hydrogen carbonate ion and/or a carbon dioxide gas to the culture medium used for the culturing enhances the enzymatic activity of, for example, phosphoenolpyruvate carboxylase, pyruvate carboxylase and/or phosphoenolpyruvate carboxykinase, and increases the amount of carbon dioxide fixed, whereby acetyl-CoA or a useful metabolite derived from acetyl-CoA can efficiently be produced.

The carbonate ion or the hydrogen carbonate ion may be derived from substance capable of generating a carbonate ion and/or a hydrogen carbonate ion when supplied to the culture medium. Examples of substances capable of generating a carbonate ion and/or a hydrogen carbonate ion include sodium carbonate, sodium hydrogen carbonate, potassium carbonate, potassium hydrogen carbonate, ammonium carbonate, ammonium hydrogen carbonate, magnesium carbonate and calcium carbonate.

The amount of carbonate ions and/or hydrogen carbonate ions supplied to the culture medium is not particularly limited as long as acetyl-CoA or a useful metabolite derived from acetyl-CoA can efficiently be produced. Carbonate ions and/or hydrogen carbonate ions are preferably supplied in a total amount of 150 mmol or more per 1 L of the culture medium. Supply of carbonate ions and/or hydrogen carbonate ions in an amount of 150 mmol/L or more sufficiently increases the yield of acetyl-CoA or the like, and thus is preferable. Carbonate ions and/or hydrogen carbonate ions are more preferably supplied in a total amount of 200 mmol or more per 1 L of the culture medium.

The total amount of carbonate ions and/or hydrogen carbonate ions supplied is preferably 5 mol or less per 1 L of the culture medium. When the total supply amount per 1 L of the culture medium is 5 mol or less, it is less likely that carbonate ions and hydrogen carbonate ions that are not used by the microorganism are present in a large amount in the culture process. The total amount of carbonate ions and/or hydrogen carbonate ions supplied per 1 L of the culture medium is more preferably 3 mol or less, and still more preferably 2 mol or less.

The method for supplying carbonate ions and/or hydrogen carbonate ions to the culture medium may be a method known in the art. The carbonate ions and/or hydrogen carbonate ions may be supplied at the time of starting the culturing or during the culturing, and the stage at which the carbonate ions and/or hydrogen carbonate ions are supplied is not particularly limited. The carbonate ions and/or hydrogen carbonate ions may be supplied all at once, or supplied multiple times in portions.

The carbon dioxide gas may be any gas that contains carbon dioxide, and may be, for example, air. The carbon dioxide concentration of the carbon dioxide gas is preferably equal to or higher than the air's carbon dioxide concentration, more preferably 0.1 v/v (volume/volume) % or higher, and still more preferably 1 v/v % or higher.

The carbon dioxide concentration is preferably 75 v/v % or lower, more preferably 50 v/v % or lower, and still more preferably 25 v/v % or lower.

The carbon dioxide gas can be dissolved in the culture medium by bubbling, etc. The average bubble diameter of the carbon dioxide gas supplied into the culture medium is not particularly limited as long as acetyl-CoA or a useful metabolite derived from acetyl-CoA can efficiently be produced.

The carbon dioxide gas preferably has an average bubble diameter of, for example, 100 μm or more. A carbon dioxide gas having an average bubble diameter of 100 μm or more is preferable since, with an average bubble diameter within this range, it is unlikely that continuation of fermentative culturing is made difficult by excessive increase of bubbling in the culture medium. A carbon dioxide gas having an average bubble diameter of 200 μm or more is more preferable, and a carbon dioxide gas having an average bubble diameter of 500 μm or more is still more preferable. However, the average bubble diameter of the carbon dioxide gas is preferably 100 cm or less. An average bubble diameter of 100 cm or less is preferable since, with an average bubble diameter within this range, carbon dioxide sufficiently dissolves in the culture medium. A carbon dioxide gas having an average bubble diameter of 50 cm or less is more preferable, and a carbon dioxide gas having an average bubble diameter of 20 cm or less is still more preferable.

The carbon dioxide gas may be supplied to the culture medium, using a usually-employed bubble generator. Examples of bubble generators include an air sparger.

Examples of methods for measuring the average bubble diameter include LS 13 320 (manufactured by Beckman Coulter Inc.), which measures an average bubble diameter using a laser diffraction scattering method, Multisizer 3 (manufactured by Beckman Coulter Inc), which measures an average bubble diameter using a pore electric resistance method, and a method of taking a shaded image using a high-speed video camera, and obtaining an average bubble diameter via binary image processing.

The reducing agent is not particularly limited as long as the reducing agent is capable of reducing components in the culture medium or in the microorganism during culturing while the reducing agent itself is oxidized. Examples thereof include sulfur-containing compounds, carbon compounds, hydrogen, etc.

Examples of sulfur-containing compounds include sulfites (such as sodium sulfite, sodium hydrogen sulfite, potassium sulfite and ammonium sulfite), thiosulfates (such as sodium thiosulfate and potassium thiosulfate), salts of sulfide ions (such as sodium sulfide, sodium hydrogen sulfide, potassium sulfide and ammonium sulfide), cysteine, sulfur dioxide and hydrogen sulfide.

Examples of carbon-containing compounds include alcohols, fatty acids, paraffin and carbon monooxide.

Examples of preferable reducing agents include sulfur-containing compounds, and, among them, sodium sulfite, sodium hydrogen sulfite, sodium sulfate and cysteine are preferable, and sodium sulfite is most preferable.

The concentration of reducing agent supplied to the culture medium is not particularly limited as long as acetyl-CoA or a useful metabolite derived from acetyl-CoA can efficiently be produced, and may be set, as appropriate, in accordance with the components to be supplied. For example, the concentration of sodium sulfite is preferably 0.01 g or more, more preferably 0.1 g or more, and still more preferably 1 g or more, per 1 L of culture medium. The concentration of reducing agent to be supplied is preferably 50 g/L or lower, more preferably 20 g/L or lower, and still more preferably 10 g/L or lower.

The method of producing acetyl-CoA or glutamic acid may further include collecting a carbon dioxide-containing gas generated by the culturing, and supplying the gas to the culture medium used for the culturing (hereinafter referred to as "gas supply process"). In other words, the carbon dioxide gas discharged as exhaust rather than being consumed in the culture medium may be recycled through circulation by being re-supplied to the culture medium.

The method employed for supplying the gas to the culture medium is not particularly limited as long as it is a method usually employed for such a purpose. Examples thereof include: a method of injecting a gas, by pressurization, into a liquid through a circular or rectangular fine pore (, which is referred to as "aerator" or "aeration" in a case in which the gas is air); a method of supplying a gas from a hollow pipe having pores all over the circumferential face thereof (which is called "draft tube"); and a method of using an air sparger (gas diffuser), which is a plastic or stainless-steel tube having a porous material having numerous pores for generating minute bubbles of air or the like attached to an end portion of the tube.

The content of the acetyl-CoA-producing microorganism in the medium varies depending on the type and the activity of the microorganism, and the amount of the suspension of the pre-cultured microorganism to be initially fed in the culture may be 0.1% by mass to 30% by mass with respect to the culture liquid, preferably 1% by mass to 10% by mass in view of controlling culture conditions.

The medium to be used for culturing the acetyl-CoA-producing microorganism is not restricted as long as it is a normal medium containing a carbon source, nitrogen source and inorganic ion, as well as inorganic micronutrients, nucleic acids and vitamins required by the microorganism for production of the product of interest.

The culture conditions in the culturing step are not restricted, and, for example, the culture may be carried out under aerobic conditions while the pH and the temperature are appropriately controlled within the ranges of pH 4 to 9, preferably pH 6 to 8, and 20° C. to 50° C., preferably 25° C. to 42° C.

The aeration rate of the mixture is not restricted, and, when only the air is used as the gas, the aeration rate is generally 0.02 vvm to 2.0 vvm (vvm: aeration volume [mL]/liquid volume [mL]/time [minutes]) at 50 to 600 rpm. In view of suppressing physical damage to the microorganism, the aeration is carried out preferably at 0.1 vvm to 2.0 vvm, more preferably at 0.1 vvm to 1.0 vvm.

The culturing step may be continued from the beginning of the culture until the carbon source material in the mixture has been consumed, or until the activity of the acetyl-CoA-producing microorganism disappears. The time period of the culturing step varies depending on the number and the activity of the acetyl-CoA-producing microorganism in the mixture, and on the amount of the carbon source material. In general, the time period may be not less than 1 hour, preferably not less than 4 hours. By additionally feeding the carbon source material and/or the acetyl-CoA-producing microorganism, the culture period can be extended without limitation, but, in view of the treatment efficiency, the culture period may be generally not more than 5 days, preferably not more than 72 hours. In terms of other conditions, those used in normal culture may be applied as they are.

The method for recovering the product of interest accumulated in the culture liquid is not restricted, and examples of the method which may be employed include a method wherein microorganism cells are removed from the culture liquid by centrifugation or the like, followed by separating the product of interest by a normal separation method such as crystallization or chromatographic separation or membrane separation under conditions dependent on the type of the product of interest.

The method of the present invention for producing acetyl-CoA may include, before the culturing step, a pre-culturing step for appropriately adjusting the number of cells and/or the activity state of the acetyl-CoA-producing microorganism used. The pre-culturing step is not restricted as long as it is a culture under conditions normally employed depending on the type of the acetyl-CoA-producing microorganism.

The method for producing glutamic acid of the present invention includes using the acetyl-CoA-producing microorganism to produce glutamic acid as the product of interest from a carbon source material. That is, the method for producing glutamic acid includes: bringing the acetyl-CoA-producing microorganism into contact with a carbon source material and performing culture (hereinafter referred to as the culturing step); and recovering the product of interest (glutamic acid) obtained by the contact (hereinafter referred to as the recovering step).

According to the method for producing glutamic acid, since the acetyl-CoA-producing microorganism is brought into contact with a carbon source material when the microorganism is cultured, the carbon source material is assimilated by the acetyl-CoA-producing microorganism, and the product of interest can be efficiently produced while carbon dioxide is fixed.

The medium to be used for the culture is not restricted as long as it is a normal medium containing a carbon source, nitrogen source and inorganic salts, as well as organic micronutrients such as amino acids and vitamins, as required. Either a synthetic medium or natural medium may be used. The carbon source and nitrogen source used in the medium may be of any types as long as the sources can be utilized by the strain to be cultured.

Examples of the carbon source material which may be used include sugars such as glucose, glycerol, fructose, sucrose, maltose, mannose, galactose, starch hydrolysates and molasses. Organic acids such as acetic acid and citric acid, and alcohols such as ethanol may also be used alone or in combination with other carbon sources.

Examples of the nitrogen source which may be used include ammonia; ammonium salts such as ammonium sulfate, ammonium carbonate, ammonium chloride, ammonium phosphate and ammonium acetate; and nitric acid salts.

Examples of the organic micronutrients which may be used include amino acids, vitamins, fatty acids and nucleic acids; and peptones, casamino acids, yeast extracts and soybean protein hydrolysates containing these micronutrients. When an auxotrophic mutant strain that requires an amino acid(s) and/or the like for growth is used, the required nutrient(s) is/are preferably supplemented.

Examples of the inorganic salts which may be used include phosphoric acid salts, magnesium salts, calcium salts, iron salts and manganese salts.

The culture is preferably carried out at a fermentation temperature of 20 to 45° C. at a pH of 3 to 9 under aeration. For adjusting the pH, an inorganic or organic, acidic or alkaline substance, ammonia gas, and/or the like may be used. Under such conditions, L-amino acid is preferably accumulated in the culture liquid or in the cells after culturing the microorganism for 10 hours to 120 hours.

Further, when the L-amino acid of interest is L-glutamic acid, the culture may be carried out using a liquid medium whose conditions were adjusted such that L-glutamic acid is likely to be precipitated, while allowing production and accumulation of L-glutamic acid in the medium by precipitation. Examples of the conditions that allow precipitation of L-glutamic acid include pH 5.0 to 4.0, preferably pH 4.5 to 4.0, more preferably pH 4.3 to 4.0, especially preferably pH 4.0. For achieving both increased growth and efficient precipitation of L-glutamic acid under acidic conditions, the pH is preferably 5.0 to 4.0, more preferably 4.5 to 4.0, still more preferably 4.3 to 4.0. The culture at the above-described pH may be carried out either through the whole culture period or during a part of the culture period.

The L-amino acid may be collected from the culture liquid after completion of the culture according to a known collection method. For example, the collection may be carried out by a method wherein concentration crystallization is carried out after removal of the cells from the culture liquid, or by ion-exchange chromatography. When the culture was carried out under conditions that allow precipitation of L-glutamic acid in the medium, the L-glutamic acid precipitated into the culture liquid can be collected by centrifugation, filtration or the like. In such cases, L-glutamic acid remaining dissolved in the medium may be crystallized, and the crystallized L-glutamic acid may be isolated together.

EXAMPLES

The present invention is described in detail by way of Examples below. However, the present invention is not restricted by the Examples.

Example 1

Preparation of Plasmid pMWGKC

In order to obtain the GAPDH promoter, PCR amplification was carried out using genomic DNA of the *Escherichia coli* MG1655 strain as a template, and primers CGAGCTACATATGCAATGATTGACACGATTCCG (SEQ ID NO: 1) and CGCGCGCATGCTATTTGTTAGTGAATAAAAGG (SEQ ID NO: 2). The amplified DNA fragment was digested with the restriction enzymes NdeI and SphI, to obtain a DNA fragment of about 110 bp corresponding to the GAPDH promoter. The obtained DNA fragment was mixed with the fragment obtained by digesting the plasmid pBR322 (GenBank accession number J01749) with the restriction enzymes NdeI and SphI, and the fragments were ligated together using ligase. Thereafter, competent cells of the *Escherichia coli* DH5α strain (Toyobo Co., Ltd., DNA-903) were transformed with the resulting ligation product, and transformants growing on an LB agar plate supplemented with 50 μg/mL ampicillin were obtained. The obtained colonies were cultured in LB broth supplemented with 50 μg/mL ampicillin at 37° C. overnight, and the plasmid pBRgapP was recovered from the obtained bacterial cells.

Subsequently, PCR amplification was carried out using pBRgapP as a template, and primers CCGCTCGAGCATATGCTGTCGCAATGATTGACACG (SEQ ID NO: 3) and GCTATTCCATATGCAGGGTTATTGTCTCATGAGC (SEQ ID NO: 4). The amplified DNA fragment was phosphorylated using T4 Polynucleotide Kinase (Takara), to obtain a DNA fragment containing a GAPDH promoter. Further, the plasmid pMW119 (GenBank accession number AB005476) was treated with the restriction enzymes AatII and NdeI, and the ends of the digested DNA fragment were blunt-ended with KOD plus DNA polymerase (Takara), to obtain a DNA fragment having the origin of replication of pMW119. The DNA fragments containing a GAPDH promoter and the origin of replication of pMW119 were ligated together using ligase. Thereafter, competent cells of the *Escherichia coli* DH5α strain were transformed with the resulting ligation product, and transformants growing on an LB agar plate supplemented with 50 μg/mL ampicillin were obtained. An obtained colony was cultured in LB broth supplemented with 50 μg/mL ampicillin at 37° C. overnight, and the plasmid pMWG was recovered from the obtained bacterial cells.

In order to obtain a chloramphenicol resistance gene, PCR amplification was carried out using pTH18cs1 (GenBank accession No. AB019610) as a template, and primers TCGGCACGTAAGAGGTTCC (SEQ ID NO: 5) and CGGGTC-GAATTTGCTTTCG (SEQ ID NO: 6), and the obtained DNA fragment was phosphorylated using T4 Polynucleotide Kinase (Takara), to obtain a DNA fragment containing a chloramphenicol resistance gene. Subsequently, PCR amplification was carried out using pMWG as a template, and primers CTAGATCTGACAGTAAGACGGGTAAGCC (SEQ ID NO: 7) and CTAGATCTCAGGGTTATTGTCTCATGAGC (SEQ ID NO: 8). The resulting fragment was mixed with the DNA fragment containing a chloramphenicol resistance gene and ligated together using ligase. Competent cells of the *Escherichia coli* DH5α strain were transformed with the resulting ligation product, to obtain transformants growing on an LB agar plate supplemented with 25 μg/mL chloramphenicol. An obtained colony was cultured in LB broth supplemented with 25 μg/mL chloramphenicol at 37° C. overnight, and the obtained plasmid was designated pMWGC.

PCR amplification was carried out using the pMWGC gene as a template, and primers CCTTTGGTTAAAGGCTTTAAGATCTTCCAGTGGACAAACTATGCC (SEQ ID NO: 9) and GGCATAGTTTGTCCACTGGAAGATCTTAAAGCCTTTAACCAAAGG (SEQ ID NO: 10), followed by performing transformation of competent cells of the *Escherichia coli* DH5α strain. Thereafter, transformants growing on an LB agar plate supplemented with 25 μg/mL chloramphenicol were obtained. An obtained colony was cultured in LB broth supplemented with 25 μg/mL chloramphenicol at 37° C. overnight, and the plasmid pMWGKC was recovered from the obtained bacterial cells.

Example 2

Construction of Plasmid for Expression of Malate Thiokinase and Malyl-CoA Lyase Derived from *Methylococcus capsulatus* ATCC 33009

Genomic DNA of *Methylococcus capsulatus* ATCC 33009D-5 was purchased from ATCC. PCR was carried out using the chromosomal DNA of *Methylococcus capsulatus* as a template, and primers GGAATTCCATATGGCTGTTAAAAATCGTCTAC (SEQ ID NO: 11) and GCTCTAGATCAGAATCTGATTCCGTGTTC (SEQ ID NO: 12) to obtain a mcl-mtk fragment of *Methylococcus*. The fragment was digested with NdeI and XbaI and ligated to the DNA fragment obtained by digesting the plasmid pMWGKC prepared in Example 1 with NdeI and XbaI. The thus obtained plasmid was designated as pMWGKC_mcl-(Mc)_mtk(Mc).

The pMWGKC_mcl(Mc)_mtk(Mc) plasmid has the mcl gene sequence (SEQ ID NO: 13), mtkA gene (SEQ ID NO: 14) and mtkB gene (SEQ ID NO: 15) derived from *Methylococcus capsulatus*. The amino acid sequence of mcl, the amino acid sequence of mtkA and the amino acid sequence of mtkB derived from *Methylococcus capsulatus* are as shown in SEQ ID NO: 16, SEQ ID NO: 17 and SEQ ID NO: 18, respectively.

Example 3

Construction of *Pantoea Ananatis* PA Strain

The plasmid RSFCPG was recovered from *Pantoea ananatis* AJ13601 (bacterial strain BP-7207, patent deposition). The plasmid RSFCPG is a tetracycline resistance plasmid having the enzymes glutamate dehydrogenase, citrate synthase and phosphoenolpyruvate carboxylase that catalyze the biosynthetic reaction of L-glutamic acid (JP 2001-333769 A). *Pantoea ananatis* AJ417 (bacterial strain BP-8646, patent deposition) was transformed with RSFCPG using the $CaCl_2$ method (Molecular Cloning, 3rd edition, Cold Spring Harbor press, 2001), and cultured in LB broth supplemented with 10 μg/mL tetracycline, to obtain *Pantoea ananatis* AJ417/RSFCPG (which may be hereinafter abbreviated as the PA strain).

Example 4

Construction of *Pantoea Ananatis* Strains for Evaluation

The *Pantoea ananatis* PA strain prepared in Example 3 was transformed with plasmids pMWGKC described in Example 1 and pMWGKC_mcl(Mc)_mtk(Mc) described in Example 2 by electroporation. Transformants were screened on LB agar medium supplemented with 30 μg/mL chloramphenicol and 10 μg/mL tetracycline, and the obtained colonies were used as the strains for evaluation. The constructed strains are summarized in Table 1.

TABLE 1

| Strain name | Plasmid/strain | Characteristics |
|---|---|---|
| PA/pMWGKC | pMWGKC/RSFCPG/ *P. ananatis* AJ417 | No mtk or mcl overexression |
| PA/pMWGKC-mtk-mcl | pMWGKC_mcl(Mc)_mtk(Mc)/ RSFCPG/*P. ananatis* AJ417 | With overexpressed mtk and mcl |

Example 5

Glutamic Acid Production by Constructed Strains of *Pantoea Ananatis*

For the evaluation of glutamic acid production rate and yield by the constructed *Pantoea ananatis* strains described in Table 1, each of the *Pantoea* strains was first pre-cultured in 30 ml medium taken in 125-ml capacity conical flask equipped with baffles. The pre-culture medium was composed of 25 g/L LB, 0.5 g/L glucose, 0.5 g/L $MgSO_4.7H_2O$, 3 g/L $KH_2PO_4$, 0.5 g/L NaCl, 1 g/L $NH_4Cl$, 6 g/L $Na_2HPO_4$, 0.2 g/L calcium pantothenate, 0.2 g/L L-lysine hydrochloride, 0.2 g/L L-methionine and 0.2 g/L 2,6-diaminopimelic acid. Antibiotics were supplemented as per requirement at the concentration of 30 μg/mL chloramphenicol and 10 μg/mL tetracycline. The pre-culture media were inoculated from glycerol stocks of the strains and grown at 34° C. in a rotary incubator with shaking at the rate of 200 rpm for 2 days. Appropriate volumes of the pre-cultures were centrifuged at 6000 rpm and 25° C. for 15 min and their supernatant medium was discarded. The cell pellets were inoculated to 5 ml of fermentation media taken in 125-ml capacity conical flasks equipped with baffles to achieve a starting cell density ($OD_{600}$) value in the range of 0.2-0.25. The fermentation medium (pH 7) was composed of 50 g/L glucose, 20 g/L $(NH_4)_2SO_4$, 0.5 g/L $MgSO_4.7H_2O$, 2 g/L $KH_2PO_4$, 0.5 g/L NaCl, 0.25 g/L $CaCl_2.2H_2O$, 20 mg/L $FeSO_4.7H_2O$, 20 mg/L $MnSO_4.H_2O$, 0.72 mg/L $ZnSO_4.7H_2O$, 0.64 mg/L $CuSO_4.5H_2O$, 0.72 mg/L $CoCl_2.6H_2O$, 0.4 mg/L boric acid, 1.2 mg/L $(NH_4)_6Mo_7O_{24}.4H_2O$, 2 g/L yeast extract, 0.2 g/L calcium pantothenate, 0.2 g/L L-lysine hydrochloride, 0.2 g/L L-methionine, 0.2 g/L 2,6-diaminopimelic acid and 20 g/L calcium carbonate. Antibiotics were supplemented as per requirement at the concentration of 30 μg/mL chloramphenicol and 10 μg/mL tetracycline. The optical density ($OD_{600}$) was measured at 600 nm after diluting the fermentation samples with 2 N HCl. Glutamic acid fermentation was conducted at 34° C. in a rotary incubator with shaking at the rate of 250 rpm for 48 hours. Samples were withdrawn at periodic intervals and analyzed by High Performance Liquid Chromatography (HPLC). Glucose consumption was monitored using Ultron PS-80H column (Shinwa Chemical Industries Ltd., Japan) operated under standard conditions while glutamic acid production was estimated using the RSpak NN-814 column (Showa Denko K. K., Japan) operated under standard conditions. The results of the comparison of fermentation performance of the constructed *Pantoea* strains after 48 hours of fermentation are summarized in Table 2.

TABLE 2

| Strain name | Glutamic acid titer (g/L) | Glutamic acid yield (g/g) | Cell growth (OD600) |
|---|---|---|---|
| PA/pMWGKC | 25.15 | 0.40 | 25.4 |
| PA/pMWGKC-mtk-mcl | 33.66 | 0.54 | 16.6 |

[1]Fermentation time was 48 hours
[2]Results shown are average of three replicate experiments The data in Table 2 shows that overexpression of mtk and mcl in *Pantoea* resulted in almost 35% higher glutamic acid production and yield compared to the control strain without mtk and mcl. Such a significant yield improvement can help to reduce the overall glutamic acid production costs and substantially improve the efficiency of the process. Additionally, an unexpected observation was that the biomass formation in the mtk and mcl-overexpressing strain was significantly lower than the control strain in spite of which the glutamic acid production was enhanced. This suggests that the engineered mtk and mcl-overexpressing strain can more efficiently consume the carbon source to produce glutamic acid at higher rate and yield when compared to the control strain. Low biomass formation during fermentation is also advantageous for an industrial process in terms of reduced generation of biological waste which otherwise needs to be recycled or disposed.

Example 6

Evaluation of Additive

Culturing and analysis were carried out in the same manner as in Example 5, except that the PA/pMWGKC-mtk-mcl constructed in Example 4 is used as a variant to be evaluated, and that a carbonate salt, a carbon dioxide gas or a reducing agent is supplied, as an additive, to the culture medium.

As the result of the analysis, the groups supplied with a carbonate gas, a carbon dioxide gas and a reducing agent, respectively, exhibited higher yield per sugar than a group supplied with none of a carbonate salt, a carbon dioxide gas or a reducing agent (a group in which the PA/pMWGKC-mtk-mcl constructed in Example 4 is used as a variant to be evaluated without supply of any of a carbonate salt, a carbon dioxide gas or a reducing agent).

Thus, it is indicated that, in the *Pantoea* strain to which a $CO_2$ fixation pathway is imparted, supply of a carbonate salt, a carbon dioxide gas or a reducing agent is effective in terms of heightening the yield per sugar.

Example 7

Preparation of Plasmid pMWGKC2

In order to obtain the GAPDH promoter, PCR amplification was carried out using genomic DNA of the *Escherichia coli* MG1655 strain as a template, and primers CTACTAGTCTGTCGCAATGATTGACACGATTCCG (SEQ ID NO: 19) and GCTCGAATTCCCATATGTTCCACCAGCTATTTGTTAGTGAATAAAAGG (SEQ ID NO: 20). The amplified DNA fragment was digested with the restriction enzyme EcoRI. The DNA fragment was phosphorylated using T4 Polynucleotide Kinase (Takara), to obtain a DNA fragment containing a GAPDH promoter. Further, the plasmid pMW119 (GenBank accession number AB005476) was treated with the restriction enzyme NdeI, and the ends of the digested DNA fragment were blunt-ended with KOD plus DNA polymerase (Takara), and the fragment was treated with the restriction enzyme EcoRI to obtain a DNA fragment having the origin of replication of pMW119. The DNA fragments containing a GAPDH promoter and the origin of replication of pMW119 were ligated together using ligase. Thereafter, competent cells of the *Escherichia coli* DH5α strain were transformed with the resulting ligation product, and transformants growing on an LB agar plate supplemented with 50 μg/mL ampicillin were obtained. An obtained colony was cultured in LB broth supplemented with 50 μg/mL ampicillin at 37° C. overnight, and the plasmid pMWG2 was recovered from the obtained bacterial cells.

In order to obtain a chloramphenicol resistance gene, PCR amplification was carried out using pTH18cs1 (GenBank accession No. AB019610) as a template, and primers TCGGCACGTAAGAGGTTCC (SEQ ID NO: 5) and CGGGTCGAATTTGCTTTCG (SEQ ID NO: 6), and the obtained DNA fragment was phosphorylated using T4 Polynucleotide Kinase (Takara), to obtain a DNA fragment containing a chloramphenicol resistance gene. Subsequently, PCR amplification was carried out using pMWG2 as a template, and primers CTAGATCTGACAGTAAGACGGGTAAGCC (SEQ ID NO: 7) and CTAGATCTCAGGGTTATTGTCTCATGAGC (SEQ ID NO: 8). The resulting fragment was mixed with the DNA fragment containing a chloramphenicol resistance gene and ligated together using ligase. Competent cells of the *Escherichia coli* DH5α strain were transformed with the resulting ligation product, to obtain transformants growing on an LB agar plate supplemented with 25 μg/mL chloramphenicol. An obtained colony was cultured in LB broth supplemented with 25 μg/mL chloramphenicol at 37° C. overnight, and the obtained plasmid was designated as pMWGC2.

PCR amplification was carried out using the pMWGC2 gene as a template, and primers CCTTTGGTTAAAGGCTTTAAGATCTTCCAGTGGACAAACTATGCC (SEQ ID NO: 9) and GGCATAGTTTGTCCACTGGAAGATCTTAAAGCCTTTAACCAAAGG (SEQ ID NO: 10), followed by performing transformation of competent cells of the *Escherichia coli* DH5α strain. Thereafter, transformants growing on an LB agar plate supplemented with 25 μg/mL chloramphenicol were obtained. An obtained colony was cultured in LB broth supplemented with 25 μg/mL chloramphenicol at 37° C. overnight, and the plasmid pMWGKC2 was recovered from the obtained bacterial cells.

Example 8

Glutamic Acid Production by Constructed Strains of *Pantoea ananatis* by Using pMWGKC2 Vector In the same manner as Example 2, the mcl-mtk fragment of *Methylococcus* was inserted into pMWGKC2, and the obtained plasmid was designated as pMWGKC2_mcl(Mc)_mtk(Mc). In the same manner as Example 4, the *Pantoea ananatis* PA strain was transformed with plasmids pMWGKC2 and pMWGKC2_mcl(Mc)_mtk(Mc), and the obtained strains were designated as PA/pMWGKC2 and PA/pMWGKC-mtk-mcl2, respectively. Glutamic acid production was evaluated by the method described in Example 5, to show the same trends of the glutamic acid titer, yield and cell growth as shown in Table 2.

Culturing and analysis were carried out in the same manner as in Example 6, and a carbonate salt, carbon dioxide gas or a reducing agent was supplied, as an additive, to the culture medium. Based on the result of the analysis, the groups supplied with a carbonate salt, carbon dioxide gas and a reducing agent, respectively, exhibited higher yield per sugar than the group without addition of any carbonate salt, carbon dioxide gas or any reducing agent (a group in which the PA/pMWGKC-mtk-mcl2 is used as a variant to be evaluated without supply of any of a carbonate salt, carbon dioxide gas or a reducing agent).

The entire disclosures of Japanese Patent Application No. 2013-011535 applied on 24 Jan. 2013 are hereby incorporated by reference.

All the literature, patent literature, and technical standards cited herein are also herein incorporated to the same extent as provided for specifically and severally with respect to an individual literature, patent literature, and technical standard to the effect that the same should be so incorporated by reference.

---

The invention claimed is:

1. An acetyl-CoA-producing microorganism of the genus *Pantoea* in which malate thiokinase and malyl-CoA lyase enzymatic activities are imparted to the microorganism by a gene recombination technology comprising introducing genes encoding said malate thiokinase and malyl-CoA lyase into said microorganism, and wherein said microorganism has none of the following cycles of (a), (b), (c), and (d) and without imparting any of (a), (b), (c), and (d):
   (a) a carbon dioxide fixation cycle having an enzymatic reaction from malonyl-CoA to malonate semialdehyde or 3-hydroxypropionate;
   (b) a carbon dioxide fixation cycle having an enzymatic reaction from acetyl-CoA and $CO_2$ to pyruvate;
   (c) a carbon dioxide fixation cycle having an enzymatic reaction from crotonyl-CoA and $CO_2$ to ethylmalonyl-CoA or glutaconyl-CoA; and
   (d) a carbon dioxide fixation cycle having an enzymatic reaction from $CO_2$ to formate.

2. A method of producing acetyl-CoA, comprising:
   culturing the acetyl-CoA-producing microorganism of claim 1 in contact with a carbon source material under conditions to produce said acetyl-CoA; and
   collecting said acetyl-CoA obtained by said culturing.

3. The method of producing acetyl-CoA of claim 2, further comprising:
   supplying at least one of a carbonate ion, a hydrogen carbonate ion, a carbon dioxide gas or a reducing agent to said culturing.

4. The method of producing acetyl-CoA of claim 2, further comprising:
   collecting a carbon-dioxide containing gas generated by said culturing, and supplying said gas to said culturing.

5. A method for producing glutamic acid, comprising:
   culturing the acetyl-CoA-producing microorganism of claim 1 in contact with a carbon source material under conditions to produce said glutamic acid; and
   collecting said glutamic acid obtained by said culturing.

6. The method of producing acetyl-CoA according to claim 3, further comprising:
   collecting a carbon-dioxide containing gas generated by said culturing, and supplying said gas to said culturing.

* * * * *